United States Patent
Tsukada et al.

(10) Patent No.: US 12,302,005 B2
(45) Date of Patent: May 13, 2025

(54) DETERMINATION OF LIGHT AMOUNT OF ILLUMINATION OF VISIBLE LIGHT WITH WHICH THE EYE PART IS IRRADIATED SUCH THAT PUPIL SIZE SATISFIES A SIZE CONDITION

(71) Applicant: NEC Corporation, Tokyo (JP)

(72) Inventors: Masato Tsukada, Tokyo (JP); Chisato Funayama, Tokyo (JP); Yuka Ogino, Tokyo (JP); Hiroshi Imai, Tokyo (JP); Keiichi Chono, Tokyo (JP); Emi Kitagawa, Tokyo (JP); Yasuhiko Yoshida, Tokyo (JP); Hiroshi Yamada, Tokyo (JP); Shoji Yachida, Tokyo (JP); Takashi Shibata, Tokyo (JP)

(73) Assignee: NEC CORPORATION, Tokyo (JP)

( * ) Notice: Subject to any disclaimer, the term of this patent is extended or adjusted under 35 U.S.C. 154(b) by 337 days.

(21) Appl. No.: 17/638,356

(22) PCT Filed: Sep. 4, 2019

(86) PCT No.: PCT/JP2019/034714
§ 371 (c)(1),
(2) Date: Feb. 25, 2022

(87) PCT Pub. No.: WO2021/044540
PCT Pub. Date: Mar. 11, 2021

(65) Prior Publication Data
US 2022/0294965 A1   Sep. 15, 2022

(51) Int. Cl.
*G06T 7/90* (2017.01)
*G06T 7/60* (2017.01)
(Continued)

(52) U.S. Cl.
CPC ............... *H04N 23/74* (2023.01); *G06T 7/60* (2013.01); *G06T 7/90* (2017.01); *G06V 40/18* (2022.01);
(Continued)

(58) Field of Classification Search
CPC .......... H04N 23/74; H04N 23/71; G06T 7/60; G06T 7/90; G06T 2207/10048;
(Continued)

(56) References Cited

U.S. PATENT DOCUMENTS

| 2003/0002714 A1 | 1/2003 | Wakiyama |
| 2003/0058492 A1 | 3/2003 | Wakiyama |

(Continued)

FOREIGN PATENT DOCUMENTS

| CN | 103929130 A | 7/2014 |
| CN | 106056036 A | 10/2016 |

(Continued)

OTHER PUBLICATIONS

International Search Report for PCT Application No. PCT/JP2019/034714, mailed on Oct. 21, 2019.
(Continued)

*Primary Examiner* — Ming Y Hon

(57) ABSTRACT

A control device according to an aspect of the present disclosure includes: at least one memory configured to store instructions; and at least one processor configured to execute the instructions to: acquire an input image including an eye region that is a region of an eye part; estimate illuminance of the eye part from the acquired input image; and determine a light amount of illumination of visible light with which the eye part is irradiated in such a way that a pupil size of the eye part satisfies a size condition based on an illuminance size relationship that is a relationship between the illuminance and the pupil size.

18 Claims, 14 Drawing Sheets

(51) Int. Cl.
*G06V 40/18* (2022.01)
*H04N 23/71* (2023.01)
*H04N 23/74* (2023.01)

(52) U.S. Cl.
CPC ........... *G06V 40/193* (2022.01); *H04N 23/71* (2023.01); *G06T 2207/10048* (2013.01); *G06T 2207/10152* (2013.01); *G06T 2207/30201* (2013.01)

(58) Field of Classification Search
CPC ........... G06T 2207/10152; G06T 2207/30201; G06V 40/18; G06V 40/193; G06V 10/141
See application file for complete search history.

(56) References Cited

U.S. PATENT DOCUMENTS

| | | | |
|---|---|---|---|
| 2004/0169817 | A1 | 9/2004 | Grotehusmann et al. |
| 2014/0218416 | A1 | 8/2014 | Suzuki et al. |
| 2015/0238087 | A1 | 8/2015 | Yamashita et al. |
| 2015/0254508 | A1* | 9/2015 | Kimura ................ G06V 40/197 382/117 |
| 2015/0304535 | A1* | 10/2015 | Smits .................... G06V 30/142 348/78 |
| 2016/0282934 | A1* | 9/2016 | Willis ..................... G06F 1/325 |
| 2017/0091548 | A1* | 3/2017 | Agrawal .............. G06V 10/141 |
| 2017/0255823 | A1* | 9/2017 | Abe ...................... A61B 3/0008 |
| 2017/0323167 | A1* | 11/2017 | Mapen ..................... G06T 7/90 |
| 2018/0064576 | A1* | 3/2018 | Chen ..................... A61B 3/113 |
| 2018/0096119 | A1* | 4/2018 | Yun ....................... A61B 5/024 |
| 2018/0121639 | A1* | 5/2018 | Liu ........................ G06V 40/18 |
| 2018/0125357 | A1* | 5/2018 | Suzuki .................. A61B 3/145 |
| 2018/0173933 | A1* | 6/2018 | Gousev ................ G06V 40/193 |
| 2018/0333092 | A1* | 11/2018 | Roshan ................ A61B 3/0091 |
| 2018/0357475 | A1* | 12/2018 | Honda .................. G06V 40/197 |
| 2018/0364587 | A1* | 12/2018 | Baselmans .......... G03F 7/70625 |
| 2018/0365490 | A1* | 12/2018 | Agrawal .............. G06V 40/193 |
| 2020/0042789 | A1* | 2/2020 | Perälä .................. H01L 25/0753 |
| 2020/0063938 | A1* | 2/2020 | Kurashige .............. G02B 27/30 |
| 2020/0092971 | A1* | 3/2020 | Tsubota ................ A61N 5/0613 |
| 2022/0141372 | A1* | 5/2022 | Chono ................... G06T 1/0007 348/78 |

FOREIGN PATENT DOCUMENTS

| | | |
|---|---|---|
| CN | 107408168 A | 11/2017 |
| JP | 2003-016434 A | 1/2003 |
| JP | 2003-016435 A | 1/2003 |
| JP | 2004-261515 A | 9/2004 |
| JP | 2007-125963 A | 5/2007 |
| JP | 2014-155005 A | 8/2014 |
| JP | 2018-073369 A | 5/2018 |
| WO | 2011/042989 A1 | 4/2011 |
| WO | 2014/073645 A1 | 5/2014 |
| WO | 2015/114724 A1 | 8/2015 |
| WO | 2016/080031 A1 | 5/2016 |

OTHER PUBLICATIONS

English translation of Written opinion for PCT Application No. PCT/JP2019/034714, mailed on Oct. 21, 2019.
IN Office Action for IN Application No. 202247010984, mailed on Jul. 21, 2022 with English Translation.
Extended European Search Report for EP Application No. 19944642. 8, dated on Aug. 8, 2022.
JP Office Action for JP Application No. 2023-205147, mailed on Jul. 9, 2024 with English Translation.
Chinese Office Communication for CN Application No. 201980099822. 0, mailed on Feb. 17, 2025 with English Translation.

* cited by examiner

Fig. 13

| AMOUNT OF INCIDENT LIGHT L | APERTURE VALUE F | SHUTTER SPEED S | TRISTIMULUS VALUE Y |
|---|---|---|---|
| L1 | F1 | S1 | Y1 |
| L1 | F1 | S2 | Y2 |
| L1 | F2 | S1 | Y3 |
| L1 | F2 | S2 | Y4 |
| L2 | F1 | S1 | Y5 |
| L2 | F1 | S2 | Y6 |
| L2 | F2 | S1 | Y7 |
| L2 | F2 | S2 | Y8 |

DETERMINATION OF LIGHT AMOUNT OF ILLUMINATION OF VISIBLE LIGHT WITH WHICH THE EYE PART IS IRRADIATED SUCH THAT PUPIL SIZE SATISFIES A SIZE CONDITION

This application is a National Stage Entry of PCT/JP2019/034714 filed on Sep. 4, 2019, the contents of all of which are incorporated herein by reference, in their entirety.

TECHNICAL FIELD

The present disclosure relates to a technique for controlling a device, and more particularly to a technique for controlling illumination that irradiates a person with light.

BACKGROUND ART

As a method of personal authentication by a living body, there is iris authentication in which authentication is performed using an iris image. The shape of an iris changes depending on the amount of light radiating a pupil. For example, in a dark environment, the pupil is open. In the image used for iris authentication, an iris region becomes narrow in the case where the pupil is too open. As a result, the accuracy of authentication is likely to decrease. In the case where the pupil is exposed to strong light, the pupil contracts and becomes smaller. In the case where the pupil is too small, there is a possibility that the authentication accuracy is reduced due to a failure of detection of the pupil, and a significant difference in the shape of the iris acquired as an image from the shape of the iris in the image used for authentication. Radiation of strong light that significantly reduces the iris not only causes discomfort to the user but can also damage a retina. In the iris authentication, safe and highly accurate iris authentication can be implemented by using an iris image having a pupil size included in a predetermined range.

PTL 1 describes an iris imaging device that captures an iris image suitable for personal authentication. The iris imaging device of PTL 1 estimates brightness on the basis of a captured image. In a case where an environment is dark, the iris imaging device radiates visible illumination light toward an eye direction. The iris imaging device appropriately controls a visible light emission amount and captures a plurality of iris images having different pupil sizes.

PTL 2 describes a control system that irradiates one of left and right eyes with light and controls an imaging unit to image a tail of the other eye while radiating the light. PTL 4 obtains an iris image with a pupil in a desired size by reducing or increasing illumination until a pupil size reaches a desired size.

PTL 3 describes a display device that controls a light emission unit of a display device in consideration of the brightness of ambient light at the time of capture, and a control method thereof.

Patent Document 4 describes a biological information measuring device that measures biological information of an object person from luminance of at least a part of a skin region around a detected pupil region.

CITATION LIST

Patent Literature

[PTL 1] JP 2004-261515 A
[PTL 2] WO 2016/080031
[PTL 3] JP 2014-155005 A
[PTL 4] WO 2014/073645

SUMMARY OF INVENTION

Technical Problem

For example, in a case of performing iris authentication at a walk-through gate, it is necessary to quickly obtain an iris image suitable for iris authentication. In the technique of PTL 1, to obtain an appropriate iris image, it is necessary to select an appropriate iris image from the iris images captured a plurality of times. In the technique of PTL 2, it is necessary to repeat capture while changing the brightness of the illumination until an iris image with the pupil size in the desired size is obtained. With these techniques, it may not be possible to obtain an iris image with the pupil size in the desired size in a short time.

An object of the present disclosure is to provide a control device and the like that can shorten the time required to obtain an iris image in a desired state.

Solution to Problem

A control device according to one aspect of the present disclosure includes: an acquisition means configured to acquire an input image including an eye region that is a region of an eye part; an estimation means configured to estimate illuminance of the eye part from the acquired input image; and a determination means configured to determine a light amount of illumination of visible light with which the eye part is to be irradiated in such a way that a pupil size of the eye part satisfies a size condition based on an illuminance size relationship that is a relationship between the illuminance and the pupil size.

A control method according to one aspect of the present disclosure includes: acquiring an input image including an eye region that is a region of an eye part; estimating illuminance of the eye part from the acquired input image; and determining a light amount of illumination of visible light with which the eye part is to be irradiated in such a way that a pupil size of the eye part satisfies a size condition based on an illuminance size relationship that is a relationship between the illuminance and the pupil size.

A storage medium according to one aspect of the present disclosure stores a program for causing a computer to execute: acquisition processing of acquiring an input image including an eye region that is a region of an eye part; estimation processing of estimating illuminance of the eye part from the acquired input image; and determination processing of determining a light amount of illumination of visible light with which the eye part is to be irradiated in such a way that a pupil size of the eye part satisfies a size condition based on an illuminance size relationship that is a relationship between the illuminance and the pupil size.

Advantageous Effects of Invention

The present disclosure has an effect of shortening the time required to obtain an iris image in a desired state.

BRIEF DESCRIPTION OF DRAWINGS

FIG. 13 is a table schematically illustrating an example of a look-up table according to the first example embodiment of the present disclosure.

EXAMPLE EMBODIMENT

Next, example embodiments of the present disclosure will be described in detail with reference to the drawings.

First Example Embodiment

First, a first example embodiment of the present disclosure will be described in detail with reference to the drawings.

<<Configuration>>

Figure 1:
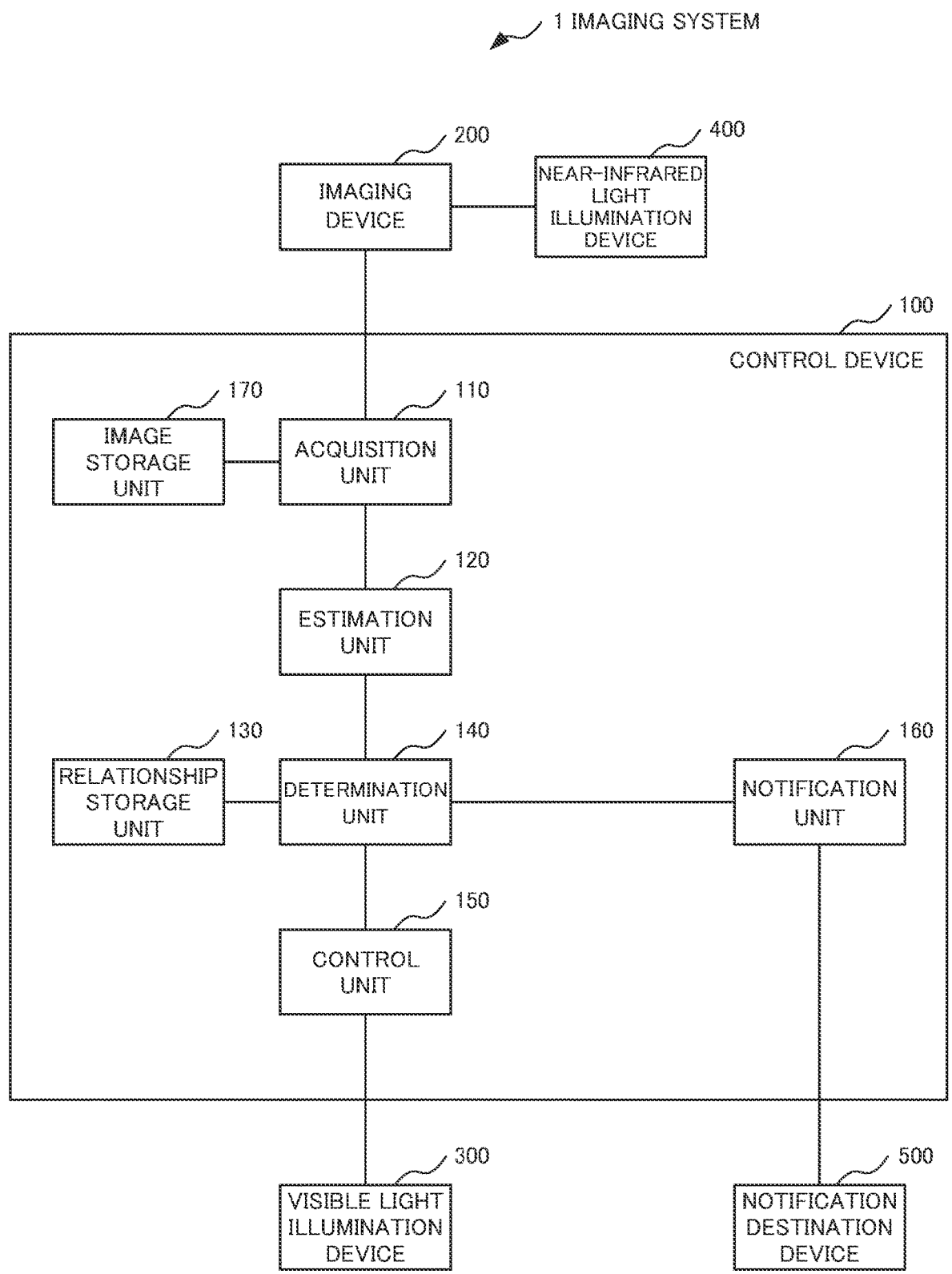
FIG. 1 is a block diagram illustrating an example of a configuration of an imaging system according to a first example embodiment of the present disclosure.

FIG. 1 is a block diagram illustrating an example of a configuration of an imaging system according to the present example embodiment.

An imaging system 1 of FIG. 1 includes a control device 100, an imaging device 200, a visible light illumination device 300, and a notification destination device 500. The imaging system 1 may further include a near-infrared light illumination device 400. In FIG. 1, the visible light illumination device 300 is drawn under the control device 100, but the actual arrangement does not have to be as in this example.

Figure 2:
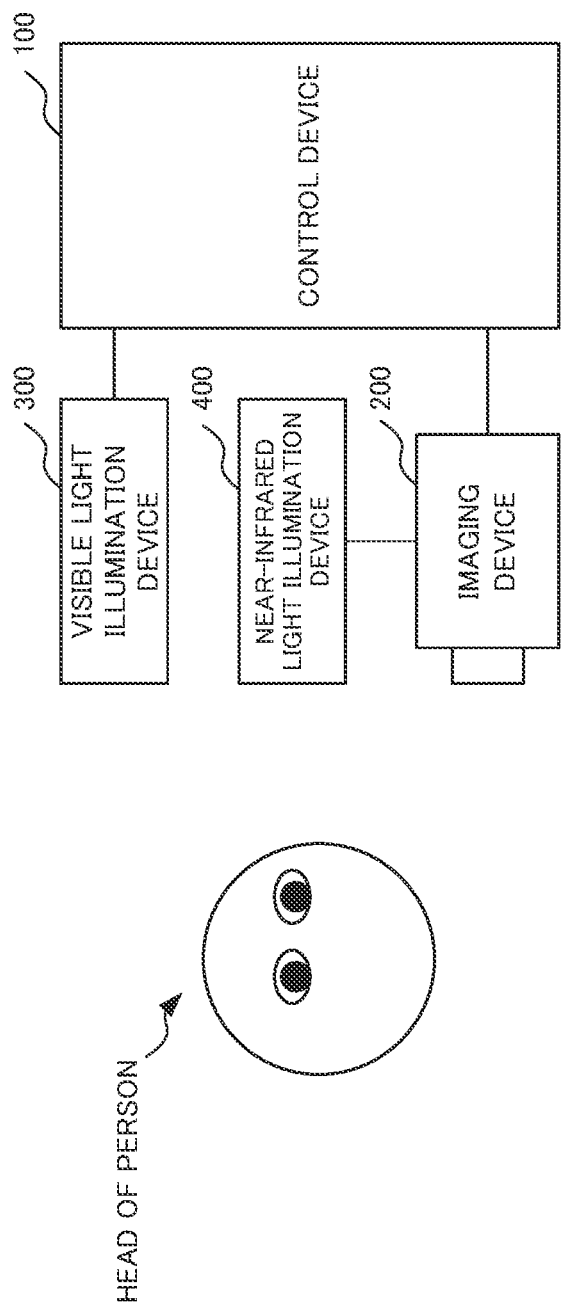
FIG. 2 is a diagram schematically illustrating an example of arrangement of an imaging device, a visible light illumination device, and a near-infrared light illumination device with respect to a person.

FIG. 2 is a diagram schematically illustrating an example of arrangement of the imaging device 200, the visible light illumination device 300, and the near-infrared light illumination device 400 with respect to a person. As illustrated in FIG. 2, the imaging device 200 may be arranged to image the head of the person. The visible light illumination device 300 may be arranged to irradiate the head of the person being imaged with visible light. The near-infrared light illumination device 400 may be arranged to irradiate the head of the person being imaged with near-infrared light. The control device 100 is communicatively connected to the imaging device 200. The control device 100 is communicatively connected to the visible light illumination device 300. The control device 100 may be installed at a location distant from the imaging device 200, the visible light illumination device 300, and the near-infrared light illumination device 400. The control device 100 may be installed adjacent to the imaging device 200, the visible light illumination device 300, and the near-infrared light illumination device 400.

The following description is given on the assumption that the person is moving by walking. However, the person may be moving by means other than walking. The person does not have to be moving.

<<Imaging Device 200>>

The imaging device 200 is a camera capable of capturing moving images and still images (hereinafter collectively referred to as images). The imaging device 200 transmits the captured image to the control device 100. The imaging device 200 may include an image sensor such as a charge coupled device (CCD) or a complementary metal oxide semiconductor (CMOS) image sensor. The image sensor of the imaging device 200 is a sensor that is sensitive to a wavelength band including at least a part of a near-infrared wavelength band (for example, 780 to 1000 nm (nanometer)). The imaging device 200 may be, for example, a visible light camera including an image sensor to which an infrared (IR) cut filter is not attached. In this case, the imaging device 200 may be a camera capable of capturing a color image. The imaging device 200 may be a camera capable of capturing a grayscale image. The imaging device 200 may be a near-infrared light camera.

The imaging device 200 may be installed in, for example, a walk-through gate or a passage. Then, the imaging device 200 may be installed to be able to image the face of a person passing through the walk-through gate or the passage (hereinafter also referred to as a walking path). The number of imaging devices 200 does not have to be one. The imaging device 200 may be implemented by a plurality of cameras that image different ranges. Specifically, the imaging device 200 may be implemented by a plurality of cameras arranged in such a way that, for example, when people of various heights walk along the walking path, the range through which the face can pass can be captured by either camera.

The imaging device 200 may be set to perform imaging in a state of a fixed focus position. The focus position is, for example, the distance from a center of the camera of the imaging device 200 to the focus position. In this case, a depth of field may be determined according to a focal length and an aperture value of the imaging device 200 and the distance from the imaging device 200 to an in-focus plane.

In the description of the present example embodiment, the depth of field of the imaging device 200 represents a range of the distance from the center of the camera of the imaging device 200 to an object considered to be in focus in the image captured by the imaging device 200. In other words, a lower limit of the depth of field of the imaging device 200 is the distance from the imaging device 200 to a closest object considered to be in focus in the image captured by the imaging device 200. An upper limit of the depth of field of the imaging device 200 is the distance from the imaging device 200 to a farthest object considered to be in focus in the image captured by the imaging device 200. The depth of field of the imaging device 200 represents the range from the above-described lower limit to the above-described upper limit. For example, in a case where the imaging device 200 captures a person in a situation where the moving person approaches the imaging device 200 from the front of the imaging device 200 with the fixed focus position, it can be considered that the object is in focus in the case where the distance to the person matches the upper limit of the distance range represented by the depth of field. In such a situation, the focus position may be set to the upper limit of the depth of field. In the case where the focus position of the imaging device 200 is fixed, an imaging range of the imaging device 200 is a range in which the distance to the imaging device 200 is included in the depth of field.

The imaging device 200 may be set to automatically focus when the object such as a person enters the imaging range. This imaging range may be a range in which the object that the imaging device 200 can focus on can exist. In that case, the imaging device 200 may be set to detect the eyes in the image obtained by imaging and to focus on the eyes when the eyes are detected. The imaging device 200 may focus on the eyes by any of various existing methods of focusing on eyes. In this case, the focus position may be the distance from the center of the camera of the imaging device 200 to the object considered to be the most strictly in focus in the image captured by the imaging device 200. The imaging device 200 may be set to perform imaging even during a focusing operation. The imaging device 200 may be set to focus on the iris of the moving person in a plurality of continuous images (frames). In other words, the imaging device 200 may be set such that the position of the iris of the person is included in the depth of field of the imaging device 200 while the imaging device 200 images the person moving within the imaging range a plurality of times.

The imaging device 200 may be set to continuously perform imaging regardless of the presence or absence of a person (for example, a pedestrian in the walking path) within the imaging range. The imaging device 200 may be set to start imaging when a person such as a pedestrian enters the imaging range and continue imaging until the moving object no longer exists in the imaging range. In that case, for example, a detection device that detects the person in the walking path using an object detection sensor implemented by a near-infrared light sensor or an ultrasonic sensor, and transmits a signal indicating detection to the imaging device 200 in the case of detecting the person may be connected to the imaging device 200. In the following description of the present example embodiment, the imaging device 200 is set to continuously perform imaging after starting the operation.

The imaging device 200 sends the image (specifically, image data) obtained by imaging to the control device 100. The image transmitted by the imaging device 200 to the control device 100 may be a moving image. The image transmitted by the imaging device 200 to the control device 100 may be a plurality of still images. The imaging device 200 further transmits camera parameters and the like at the time of imaging (hereinafter referred to as imaging information) to the control device 100. The imaging information is, for example, information such as shutter speed, aperture value, sensitivity, focal length, and focus position.

In the case where the imaging device 200 is implemented by a plurality of cameras, the imaging device 200 may send all the images captured by the plurality of cameras to the control device 100. In that case, the imaging device 200 may send a set of the image and the imaging information to the control device 100 for each camera. In the case where all the cameras included in the imaging device 200 are set to perform imaging under the same conditions and the imaging information of all the cameras is the same, the imaging device 200 may send the imaging information and the images for each camera to the control device 100.

<<Visible Light Illumination Device 300>>

The visible light illumination device 300 is an illumination that emits visible light. The visible light illumination device 300 is configured in such a way that the light amount emitted by the visible light illumination device 300 can be controlled by another device such as the control device 100. In other words, the visible light illumination device 300 is configured in such a way that the intensity of the emitted light can be changed by the control of the control device 100. The visible light illumination device 300 may be attached to illuminate an eye part imaged by the imaging device 200, of the face of a person (for example, a person walking along the walking path) imaged by the imaging device 200. Note that the eye part refers to a range including the eyes of the face of the person. Specifically, the visible light illumination device 300 is attached in such a way that the light emitted by the visible light illumination device 300 is incident on the pupil of the person imaged by the imaging device 200. The visible light illumination device 300 may be attached to the imaging device 200. The visible light illumination device 300 may be mounted to face the same direction as a direction of an optical axis of the imaging device 200. The visible light illumination device 300 may be mounted near the imaging device 200 to face a direction similar to the direction of the optical axis of the imaging device 200.

The relationship between the position and direction of the visible light illumination device 300 and the position and direction of the imaging device 200 is measured in advance and given to the control device 100.

<<Near-infrared Light Illumination Device 400>>

The near-infrared light illumination device 400 is a device that emits near-infrared light. The near-infrared light illumination device 400 may be installed to illuminate a position supposed to be imaged by the imaging device 200. The near-infrared light illumination device 400 may be configured in such a way that the intensity of the emitted near-infrared light is included within a predetermined range (for example, the intensity not to damage the retina) in a range where the face (particularly the eye part) of the person imaged by the imaging device 200 can exist. For example, in the case where the focus position of the imaging device 200 is fixed, the near-infrared light illumination device may be configured in such a way that the intensity of the emitted near-infrared light is included in a predetermined range within a range where the face of the person can pass, on a surface of the focus position. The near-infrared light illumination device 400 may be implemented by a plurality of arranged near-infrared light illumination devices. The near-infrared light illumination device 400 may be configured to continuously emit near-infrared light after the imaging system 1 starts the operation. The near-infrared light illumination device 400 may be configured to emit near-infrared light while the imaging device 200 is performing imaging. The near-infrared light illumination device 400 may be attached to the imaging device 200. The near-infrared light illumination device 400 may be attached near the imaging device 200. The near-infrared light illumination device 400 may be mounted to face a similar direction to the direction of the optical axis of the imaging device 200. The near-infrared light illumination device 400 may be configured to be connected to the above-described object detection sensor and emit near-infrared light when a moving object is detected on the walking path by the above-described object detection sensor. In the following description of the present example embodiment, the near-infrared light illumination device 400 is configured to continuously emit near-infrared light regardless of whether the imaging device 200 is performing imaging.

<<Control Device 100>>

The control device 100 includes an acquisition unit 110, an estimation unit 120, a relationship storage unit 130, a determination unit 140, a control unit 150, and a notification unit 160. The control device 100 may further include an image storage unit 170.

<<Acquisition Unit 110>>

The acquisition unit 110 acquires the image (specifically, data of the image) obtained by imaging by the imaging device 200 from the imaging device 200. The acquisition unit 110 further acquires the imaging information from the imaging device 200. In the case of acquiring a still image from the imaging device 200, the acquisition unit 110 sends the still image and the imaging information to the estimation unit 120. In the case of acquiring a moving image from the imaging device 200, the acquisition unit 110 may generate, for example, still image data for each frame from the acquired moving image data. Then, the acquisition unit 110 may send the generated still image data and the imaging information to the estimation unit 120.

The acquisition unit 110 may detect a pupil from the acquired image. In the case where the pupil is detected from the acquired image, the acquisition unit 110 may send an image of the pupil to the estimation unit 120. In the case where the pupil is not detected from the acquired image, the acquisition unit 110 does not have to send an image of the pupil to the estimation unit 120.

The acquisition unit 110 may determine whether an eye region of the acquired image is in focus. This eye region represents a region of a range including an eye of a person's face in the image. The method of determining whether the eye region of the image is in focus by the acquisition unit 110 may be any of existing methods. The acquisition unit 110 may detect, for example, a region having high contrast from the acquired image, and detect a pupil region from the detected region with high contrast. In the case where the pupil region is detected from the region with high contrast, the acquisition unit 110 may determine that the eye region is in focus. In the case where the eye region of the acquired image is in focus, the acquisition unit 110 may send the image to the estimation unit 120. In the case where the eye region of the acquired image is out of focus, the acquisition unit 110 does not have to send the image to the estimation unit 120.

In the case where the imaging device 200 is implemented by a plurality of cameras, as described above, the acquisition unit 110 receives a plurality of images captured by the plurality of cameras. In that case, the acquisition unit 110 may detect the pupil region from the plurality of received images. The acquisition unit 110 may send an image from which the pupil is detected to the estimation unit 120 and does not have to send an image from which the pupil is not detected to the estimation unit 120, among the plurality of acquired images.

The acquisition unit 110 may extract an image in which the eye region is in focus from the plurality of received images. In the case where the image in which the eye region is in focus is extracted from the plurality of received images, the acquisition unit 110 may send the extracted image in focus in the eye region to the estimation unit 120. In the case where the image in which the eye region is in focus is not extracted from the plurality of received images, the acquisition unit 110 does not have to send the image to the estimation unit 120.

The acquisition unit 110 may store the acquired images and imaging information in the image storage unit 170.

<<Estimation Unit 120>>

The estimation unit 120 receives the image (specifically, image data) and the imaging information from the acquisition unit 110. The estimation unit 120 estimates illuminance in the eye part from the received image on the basis of the received imaging information. As described above, the eye part refers to the region of the face including an eye. In the present example embodiment, the eye part includes at least an iris including a pupil and a sclera. In the present example embodiment, the illuminance of the pupil is considered to be the same as the illuminance of the eye part. In other words, in the present example embodiment, the illuminance of the pupil is considered to be the same as the illuminance of the sclera.

The estimation unit 120 first detects a scleral region of the eye from the received image. Specifically, the estimation unit 120 may extract the pupil region in the received image. The estimation unit 120 may extract the scleral region on the basis of the position of the extracted pupil. Specifically, the estimation unit 120 may detect, for example, a contour of the iris surrounding the pupil and a contour of the eye including the iris. The estimation unit 120 may extract a region brighter than the iris region between the contour of the iris and the contour of the eye as the scleral region. The method of extracting the sclera region by the estimation unit 120 is not limited to the above examples.

The estimation unit 120 further estimates the illuminance of the sclera on the basis of the imaging information and a pixel value of the sclera region. Specifically, the estimation unit 120 estimates the illuminance of the sclera on the basis of the imaging information such as sensitivity, aperture value, shutter speed, and the brightness of the sclera region represented by the pixel value of the sclera region. In the case where the sclera having given reflection characteristics is imaged under conditions represented by the received imaging information, the estimation unit 120 may estimate the illuminance of the sclera of a case of having the pixel value of the sclera extracted from the image. The reflection characteristics of the sclera may be approximately appropriately determined. For example, the estimation unit 120 may consider that a portion of the sclera other than a portion where reflection close to specular reflection occurs is a uniform diffuse reflection surface having constant reflectance. The estimation unit 120 may detect pixels brighter than a predetermined criterion in the detected sclera region as pixels of the portion where reflection close to specular reflection occurs. The estimation unit 120 may exclude the pixels detected as the pixels of the portion where reflection close to specular reflection occurs from the sclera region with the pixel value used for calculating the illuminance. Then, the estimation unit 120 may calculate the illuminance in the sclera region on the basis of the pixel value of the sclera region in the image and the reflectance of the sclera. For example, an administrator of the control device 100 may experimentally obtain the reflectance in advance and give the reflectance to the estimation unit 120. The estimation unit 120 uses the estimated sclera illuminance as the illuminance of the eye part including the pupil.

In the case where the image obtained by imaging by the imaging device 200 is a color image, the estimation unit 120 may calculate luminance of the sclera region in the color image according to a calculation method to be described below.

For example, a method of calculating the luminance of the sclera in the color image captured by a camera such as the imaging device 200 will be described. It is assumed that the pixel value of each pixel included in the color image is represented by a value of a red (R) component, a value of a green (G) component, and a value of a blue (B) component. In other words, it is assumed that the color image is composed of RGB. RGB chromaticity and white chromaticity can be specified in advance as color characteristics of the camera. The RGB chromaticity and the white chromaticity may be given to the estimation unit 120 in advance. RGB data of an RGB color system (three RGB values) are set to be uniquely converted into tristimulus values XYZ in an XYZ color system. Hereinafter, an example of a conversion method of converting RGB data into data of the tristimulus values XYZ. The relationship between the RGB of the input image and the tristimulus values XYZ is determined by, for example, the following equation (1).

[Math. 1]

$$\begin{pmatrix} X \\ Y \\ Z \end{pmatrix} = M_{RX} \begin{pmatrix} R \\ G \\ B \end{pmatrix} \quad (1)$$

In the equation (1), $M_{RX}$ is a 3×3 transformation matrix. Here, the captured image output from the camera is generally RGB to which gamma correction has been applied, but the RGB in equation (1) has a linear characteristic ($\gamma$=1.0) to which gamma correction has not been applied. The conversion equation for converting RGB to XYZ is not limited to the example of equation (1). The conversion equation may be any equation as long as the equation can uniquely convert RGB into XYZ, and may be defined as follows as a form in which a quadratic term is added, for example.

[Math. 2]

$$\begin{pmatrix} X \\ Y \\ Z \end{pmatrix} = M'_{RX} \begin{pmatrix} R \\ G \\ B \\ R^2 \\ G^2 \\ B^2 \\ R \cdot G \\ G \cdot B \\ B \cdot R \end{pmatrix} \quad (2)$$

Here, $M'_{RX}$ is a 3×9 transformation matrix.

Note that the $M_{RX}$ and $M'_{RX}$ may be calculated in advance by performing color calibration of the camera using, for example, a known color patch, and may be given to the estimation unit 120.

If information of aperture value F, shutter speed, and gain of a camera lens at the time of capture is obtained, the tristimulus value Y can be converted into absolute luminance L (cd/m$^2$).

The imaging device 200 may send the information of aperture value F, shutter speed, and gain at the time of capture to the acquisition unit 110 of the control device 100.

The acquisition unit 110 may receive the information of aperture value F, shutter speed, and gain at the time of capture from the control device 100, and send the information of aperture value F, shutter speed, and gain at the time of capture to the estimation unit 120. The estimation unit 120 may receive information of aperture value F, shutter speed, and gain at the time of capture from the acquisition unit 110. The estimation unit 120 may convert the tristimulus value Y into the absolute luminance L (cd/m$^2$) from the information of the aperture value F, the shutter speed, and the gain at the time of capture according to, for example, the method described below.

An example of a method of converting the tristimulus value Y calculated by equation (2) into the absolute luminance L (cd/m$^2$) (Candera/meter$^2$) is described. The tristimulus value Y represents a stimulus value Y among the tristimulus values XYZ. The estimation unit 120 may convert the tristimulus value Y into the absolute luminance L according to the following method. Generally, in capture with a camera, for example, the camera sets the aperture value F, shutter speed, and gain of the lens in order to obtain appropriate exposure. In the following description, it is assumed that the gain when the input image is captured is set to 1.0. That is, it is assumed that the estimation unit 120 acquires data indicating 1.0 as a gain value set when the input image is captured from the imaging device 200 via the acquisition unit 110. In this case, the tristimulus value Y corresponding to the pixel values (R, G, B) on the captured image with respect to the absolute luminance L, which is the amount of incident light on the camera, is determined by two variables of the lens aperture value F and the shutter speed.

First, the camera to be used is calibrated in advance. Specifically, in calibration, for example, a plurality of captured images is imaged while changing imaging conditions (that is, the amount of incident light (absolute luminance L (cd/m$^2$)), the lens aperture value F, and the shutter speed). From the pixel values (R, G, B) of the captured image, the tristimulus value Y is calculated by the equation (1) or the equation (2). Then, the relationship between the imaging conditions (that is, the absolute luminance L, which is the amount of incident light, the lens aperture value F, and the shutter speed) when the captured image is captured, and the tristimulus value Y obtained from the captured image is derived.

Specifically, a look-up table (LUT) may be generated as such a relationship. In this LUT, a plurality of values corresponding to the imaging conditions (that is, the absolute luminance L, the lens aperture value F, and the shutter speed S) and the tristimulus value Y calculated from the pixel values of the pixels corresponding to the location of the above-described absolute luminance L of the captured image may be associated with each other. The LUT may include a plurality of such combinations of the absolute luminance L, the lens aperture value F, the shutter speed S, and the tristimulus value Y. The LUT may be generated in such a way that the absolute luminance L is uniquely determined by the combination of the lens aperture value F, the shutter speed S, and the tristimulus value Y.

If the lens aperture value F, the shutter speed, and the tristimulus value F calculated from the pixel values of the captured image are obtained, the absolute luminance L can be obtained by this LUT. Therefore, the LUT for obtaining the absolute luminance L, which is the amount of incident light corresponding to the lens aperture value F, the shutter speed, and the tristimulus value Y, is generated by the calibration. By using the LUT, the absolute luminance L (cd/m$^2$), which is the amount of incident light at the time of capture, can be determined from the conditions at the time of capture with the camera (that is, the lens aperture value F and the shutter speed) and the tristimulus value Y corresponding to the pixel values (R, G, B) of the image captured under the conditions.

Such a LUT may be given to the estimation unit 120 in advance. The estimation unit 120 receives the input image, and the lens aperture value F and the shutter speed of when the input image has been captured. The estimation unit 120 extracts the sclera region from the input image. The estimation unit 120 calculates the tristimulus value Y from the pixel values (R, G, B) of the pixels included in the extracted sclera region. The estimation unit 120 determines the absolute luminance L, using the LUT, from the received lens aperture value and shutter speed and the calculated tristimulus value Y. The LUT may include a plurality of different combinations of absolute luminance L and tristimulus value Y for the same combination of aperture value and shutter speed.

In the case where the LUT contains a tristimulus value that matches the tristimulus value associated with the received aperture value and shutter speed and calculated from the pixel values, the estimation unit 120 specifies the absolute luminance associated with the tristimulus value in the LUT. The estimation unit 120 may use the specified tristimulus value as the absolute luminance corresponding to the tristimulus value. Note that the absolute luminance corresponding to the tristimulus value represents the absolute luminance of the object whose brightness is represented as the pixel values for which the tristimulus value is calculated.

FIG. 13 is a table illustrating an example of the LUT. An example of the LUT will be described with reference to FIG. 13. In calibration, a completely white plate is captured a plurality of times while changing the aperture value and the shutter speed. For example, eight captured images are obtained in the case of capturing the completely white plate under eight ways of conditions: the amount of light incident on the camera from the completely white plate is L1 or L2, the aperture value is F1 or F2, and the shutter speed is S1 or S2. Eight tristimulus values Y can be obtained by obtaining the tristimulus value for the pixel values of each of the obtained captured images by equation (1) or equation (2). From the eight capture conditions and the eight tristimulus values Y obtained under the eight capture conditions, the LUT as illustrated in FIG. 13 is generated. The estimation unit 120 holds, for example, the LUT as illustrated in FIG. 13 in advance.

Next, a method of calculating the amount of incident light using the LUT will be described. The estimation unit 120 calculates the tristimulus value Y from the pixel values of the received input image.

As a specific example, a case of calculating the amount of incident light L (that is, the absolute luminance L) from the input image captured in the state where the aperture value is F1 and the shutter speed is S2 will be described. The estimation unit 120 calculates a tristimulus value $Y_X$ from the pixel values of the image captured at the aperture value F1 and the shutter speed S2. Then, the estimation unit 120 extracts, from the LUT, the tristimulus value calculated from the image captured under the same capture conditions as the capture conditions of the input image (that is, the aperture value is F1 and the shutter speed is S2). In the example illustrated in FIG. 13, the tristimulus values calculated from the images captured in the state where the aperture value is F1 and the shutter speed is S2 are Y2 and Y6. The estimation unit 120 compares the tristimulus values Y2 and Y6 extracted from the LUT with the tristimulus values YX calculated from the input image. The estimation unit 120 reads the amount of incident light in the case where the tristimulus value is Y2 and the amount of incident light in the case where the tristimulus value is Y6 from the LUT. In the example illustrated in FIG. 13, the amount of incident light in the case where the tristimulus value is Y2 is L1, and the amount of incident light in the case where the tristimulus value is Y6 is L2. The estimation unit 120 calculates the amount of incident light LX by interpolation calculation that is an existing method according to a difference between the tristimulus values Y2 and Y6 extracted from the LUT and the tristimulus values YX calculated from the input image, and the amounts of incident lights L1 and L2 read from the LUT. Note that, in the example illustrated in FIG. 13, there are eight ways of capture conditions, but the number of capture conditions is not limited to eight. When creating the LUT, capture may be performed under more conditions to expand the amount of information in the LUT. By using such a LUT, a more accurate amount of incident light (that is, absolute luminance L) can be obtained.

The relationship among the amount of incident light, the lens aperture value F, the shutter speed, and the image output value may differ depending on a model and an individual difference of the camera (camera and lens if the lens can be removed from the camera). Therefore, by performing calibration for each camera (or a combination of the camera and the lens if the lens can be removed from the camera), a LUT that can convert the tristimulus value Y into highly accurate absolute luminance L ($cd/m^2$) can be generated.

Next, a method of calculating the illuminance in the sclera region will be described. The estimation unit 120 calculates apparent irradiance at each pixel position of a reflector in the image. The method described in Reference Document 1 and the method described in Reference Document 2 can be applied to the calculation of irradiance.

(Reference Document 1) Imari Sato, Yoichi Sato, and Katsushi Ikeuchi, "Estimation of Light Source Environment Based on Shadows of Objects", Information Processing Society of Japan Journal: Computer Vision and Image Media, Vol.41, No. SIG 10 (CVIM 1), December 2000.

(Reference Document 2) Takeshi Oishi, Sonoko Okura, Rei Kawakami, Takahiko Sakano, and Katsushi Ikeuchi, "Superimposition of Person Model Based on Simultaneous Capture Method of Light Source Environment and Object Using Omnidirectional Camera on MR System", Image Recognition and Understanding Symposium (MIRU2009), July 2009.

Figure 14:
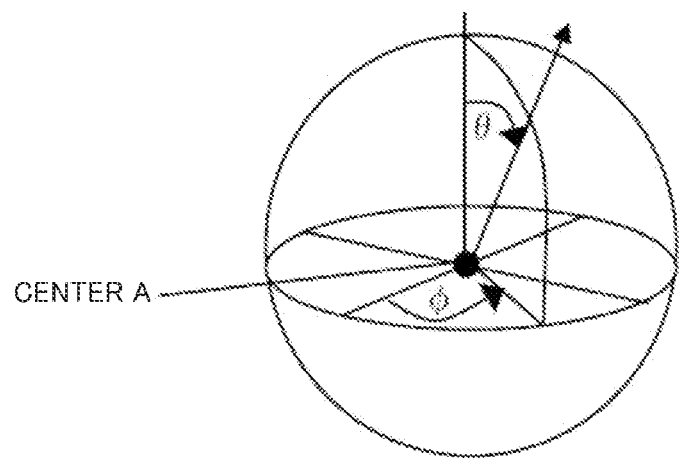
FIG. 14 is a diagram illustrating an all-around light environment model.

FIG. 14 is a diagram schematically illustrating an all-around light environment model considering a surface light source. The calculation of irradiance will be described using an all-around light environment model considering a surface light source illustrated in FIG. 14. Point A is the center of the sphere. Any point of the reflector can be selected as a center A of the sphere. In this model, a radiance distribution of the light source from all around, which is observed at the center A of the sphere, assuming that there is no obstruction blocking the light source and the center A, is modeled. The radiance distribution is L (θ, φ). Here, φ represents an azimuth angle and θ represents a zenith angle.

Illuminance $E_A$ at the center A is obtained by integrating incident light energy received from a minute solid angle $d\omega_i$ represented by a minute zenith angle $d\theta_i$ and a minute azimuth angle $d\varphi_i$ in all directions. The illuminance $E_A$ is expressed by, for example, the following equation.

[Math. 3]

$$E_A = \int_{-\pi}^{\pi}\int_0^{\frac{\pi}{2}} L_i(\theta_i, \phi_i)\cos\theta_i\sin\theta_i d\theta_i d\phi_i \quad (3)$$

Here, $d\theta_i$ represents the minute zenith angle and $d\phi_i$ represents the minute azimuth angle (i represents incident). The condition that the above equation (3) holds is that the light reflection characteristic of the reflector is Lambertian reflection. The reflection on the sclera is not necessarily Lambertian reflection. However, the situation in which the imaging device 200 images the face of a passing person corresponds to the situation in which a minute object called an eye is observed from a distance. Therefore, in the case where a point on the sclera is selected as the center A, the light reflected at the center A is an integral form of the ambient light incident on the center A from all directions, and is constant regardless of a viewpoint direction. Therefore, it can be said that equation (3) above is valid for the illuminance of the sclera. In other words, the illuminance of the sclera is approximately expressed by equation (3).

A luminance value $I_A$ in the reflector recorded as an image is expressed by a product of the illuminance $E_A$ and surface reflectance $S_A$ of the reflector, as illustrated by equation (4). The surface reflectance $S_A$ of the reflector can be obtained in advance, for example, by measurement. Here, as the luminance value $I_A$, the absolute luminance L can be used, which can be determined from the tristimulus value Y calculated by equation (1) or (2), the aperture value F of the camera lens at the time of capture, the shutter speed, the gain, and the like. The estimation unit 120 may calculate the illuminance $E_A$ by dividing $I_A$ that is the calculated absolute luminance L by the surface reflectance $S_A$ obtained in advance.

[Math. 4]

$$I_A = \int_{-\pi}^{\pi}\int_0^{\frac{\pi}{2}} S_A L_i(\theta_i, \phi_i)\cos\theta_i\sin\theta_i d\theta_i d\phi_i = S_A E_A \quad (4)$$

In the case where the luminance value is image luminance recorded by the camera, the image luminance reflects spectral sensitivity characteristics of the camera, which are expressed as a function of wavelength $\lambda$. Here, assuming that the spectral sensitivity characteristics of the camera are approximated by a delta function, the wavelength $\lambda$ can be regarded as a constant. Therefore, the image luminance $I_A^k$ (k is r, g, b) at the point A is expressed as follows. [Math. 5]

$$I_A^k = \tau^k S_A^k E_A^k \quad (5)$$

Here, $\tau^k$ is a camera gain. The estimation unit 120 may acquire the camera gain from the camera. That is, from equation (5), the illuminance $E_A^k$ at the point A can be calculated from the image luminance $I_A$ and the camera gain at the point A. It is assumed that surface reflectance $S_A^k$ (k is r, g, b) of the reflector is obtained in advance by, for example, measurement. The estimation unit 120 may calculate $E_A^k$ by dividing $I_A^k$ by $\tau^k$ and $S_A^k$. The illuminance $E_A$ of visible light is obtained by adding $E_A^r$, $E_A^g$, and $E_A^b$ as illustrated in equation (6). [Math. 6]

$$E_A = E_A^r + E_A^g + E_A^b \quad (6)$$

From the above calculation, the illuminance $E_A$ around the sclera can be obtained.

The estimation unit 120 sends the illuminance of the eye part to the determination unit 140. The estimation unit 120 may further send distance information to the determination unit 140. The distance information may be information representing the distance from the visible light illumination device 300 to the eye part in a three-dimensional space.

For example, in the case where the distance from the visible light illumination device 300 to the eye part is considered to be the same as the distance from the imaging device 200 to the eye part, the estimation unit 120 may send information indicating the distance from the imaging device 200 to the eye part to the determination unit 140 as the above-described distance information. For example, in the case where the imaging device 200 is configured in such a way that a focus distance is fixed and the distance from the imaging device 200 to the eye part is given, the estimation unit 120 may use the given distance as the distance from the visible light illumination device 300 to the eye part. In the case where the acquisition unit 110 acquires the focus distance sent from the imaging device 200, the estimation unit 120 may use the focus distance acquired by the acquisition unit 110 as the distance from the visible light illumination device 300 to the eye part.

In the case where the distance from the visible light illumination device 300 to the eye part is considered to be the same as the distance from the imaging device 200 to the eye part, the estimation unit 120 may estimate the distance from the visible light illumination device 300 to the eye part. Specifically, the estimation unit 120 may estimate the distance from the visible light illumination device 300 to the eye part on the basis of the positional relationship between the imaging device 200 and the visible light illumination device 300 and the positional relationship between the imaging device 200 and the eye part. In this case, the positional relationship between the imaging device 200 and the visible light illumination device 300 may be given in advance. Furthermore, the estimation unit 120 may calculate the positional relationship between the imaging device 200 and the eye part on the basis of the image including the region of the eye part imaged by the imaging device 200 and the imaging information of when the image including the region of the eye part is imaged by the imaging device 200.

(Modification)

Next, a modification of the estimation unit 120 will be described. In the case of calculating the absolute luminance using the LUT, the estimation unit 120 of the present modification may calculate the absolute luminance as described below. The estimation unit 120 of the present modification may operate similarly to the estimation unit 120 described above, except that the estimation unit operates as described below. In the case where the LUT does not contain a tristimulus value that matches the tristimulus value associated with the received aperture value and shutter speed and calculated from the pixel values, the estimation unit 120 extracts, for example, two tristimulus values closest to the calculated tristimulus values from the tristimulus values included in the LUT. Then, the estimation unit 120 may calculate the absolute luminance for the calculated tristimulus value from the absolute luminances associated with the extracted tristimulus values by interpolation based on the difference between the extracted tristimulus values and the calculated tristimulus value. For example, in the LUT, the two tristimulus values closest to calculated tristimulus value Ya associated with the received aperture value and shutter speed are Yb and Yc, and the absolute luminance associated with Yb is Lb and the absolute luminance associated with Yc is Lc. In this case, the estimation unit 120 may calculate target absolute luminance La corresponding to the pixels having the pixel values from which the tristimulus value Ya is derived, by, for example, an equation La=Lb+(Lc−Lb)×(Ya−Yb)/(Yc−Yb).

In the case where the LUT does not contain the tristimulus value that matches the tristimulus value associated with the received aperture value and shutter speed and calculated from the pixel values, the estimation unit 120 may select three or more tristimulus values respectively associated with the absolute luminances from the LUT. The method of selecting three or more tristimulus values may be any of various existing methods, for example, a method of excluding outliers and selecting tristimulus values. In this case, the estimation unit 120 calculates the absolute luminance L corresponding to the calculated tristimulus value Y on the basis of the selected tristimulus values. Specifically, the estimation unit 120 may derive a function representing the relationship between the tristimulus value and the absolute luminance by, for example, a least squares method. Such a function may be a predetermined type of curve (for example, a straight line). The estimation unit 120 may calculate the absolute luminance L from the calculated tristimulus value Y by the derived function.

In the case where the LUT does not include the combination of the received aperture value and shutter speed, the estimation unit 120 may calculate a combination of the absolute luminance L and the tristimulus value Y, of the case where the capture conditions are the received aperture value and shutter speed, using the LUT.

Specifically, the estimation unit 120 may first extract, from the combinations included in the LUT, a combination including the aperture value and the shutter speed, which is the closest to the received aperture value and shutter speed.

In the case where the aperture value is represented by an F value, the area of an aperture opening is halved when the aperture value is multiplied by the square root of 2. Note that the F value is a value obtained by dividing the focal length of the lens by an effective aperture. The F value may be represented by a character string consisting of the letter "F" and a decimal or integer with up to two significant figures, but here the F value is represented by a real number. In the case where the shutter speed is represented by the length of time the shutter is open, the time the shutter is open is halved when the value of the shutter speed is halved.

In the case where the optical system of the camera and the object to be captured are the same, the brightness of the object to be captured in the captured image should be the same if a sum of a squared log of the aperture value (that is, twice the log of the aperture value) and a value with an inverted sign of the log of the shutter speed are the same. In this cases, the base of the logarithm may be, for example, 2. Hereinafter, the sum of the squared log of the aperture value that is the F value and the value with an inverted sign of the log of the shutter speed represented by the length of time will be referred to as a brightness value. The smaller the brightness value, the brighter the image captured at the aperture value and the shutter speed for which the brightness value is calculated. The sign of the brightness value may be reversed.

The aperture value may be represented by, for example, the number of stages based on a predetermined aperture state. This number of stages is a numerical value representing a difference between states of two apertures by a scale factor of the area of the aperture opening. Hereinafter, the aperture state that serves as a reference is referred to as a reference state. In general, in the case where the area of the aperture opening when the aperture is in one state is $2^n$ times (or $(1/2)^n$ times) the area of the opening when the aperture is in the other state, the number of stages representing the difference between the two states is n. Here, in the case where the area of the aperture opening in a certain state (assumed to be state A) is $(1/2)^n$ times the area of the aperture opening in the reference state, the number of stages in the state A is +n. In the case where the area of the aperture opening in a certain state (assumed to be state B) is $2^n$ times the area of the aperture opening in the reference state, the number of stages in the state B is −n. In this case, the number of stages is the difference between base-2 logarithms of the two F-numbers that represent the two aperture states.

The shutter speed may also be represented by, for example, the number of stages based on a predetermined shutter speed. This number of stages is a numerical value representing a difference between two shutter speeds by a scale factor of the length of time represented by the shutter speed. Hereinafter, the shutter speed that serves as a reference is referred to as a reference shutter speed. In general, in the case where the length of time represented by one shutter speed is $2^n$ times (or $(1/2)^n$ times) the length of time represented by the other shutter speed, the number of stages representing the difference between the two shutter speeds is n. Here, in the case where the length of time represented by a certain shutter speed (referred to as shutter speed A) is $(1/2)^n$ times the length of time represented by the reference shutter speed, the number of stages of the shutter speed A is −n. In the case where the length of time represented by a certain shutter speed (referred to as shutter speed) is $2^n$ times the length of time represented by the reference shutter speed, the number of stages of the shutter speed B is −n. In this case, the number of stages is the difference between the base-2 logarithms of the two shutter speeds.

The brightness value in this case may be a value obtained by subtracting the shutter speed represented by the number of stages from a predetermined shutter speed from the aperture value represented by the number of stages from a predetermined aperture.

The estimation unit 120 may calculate the brightness value from the received aperture value and shutter speed. Hereinafter, the brightness value calculated from the received aperture value and shutter speed will be referred to as a target brightness value. The estimation unit 120 may calculate the above-described brightness value for each combination of the aperture value and the shutter speed included in the LUT. The brightness value calculated from the combination of the aperture value and the shutter speed included in the LUT will be hereinafter referred to as an LUT brightness value.

The estimation unit 120 may extract the LUT brightness value that matches the target brightness value calculated from the received aperture value and shutter speed according to the LUT brightness value.

The estimation unit 120 may extract the combinations of the aperture value and the shutter speed for which the extracted LUT brightness value is calculated from the LUT. In the case where the extracted combinations has a combination associated with the tristimulus value Y that matches the tristimulus value Y calculated from the input image, the estimation unit 120 identifies the absolute luminance associated with the combination. The estimation unit 120 determines the specified absolute luminance as the target absolute luminance.

In the case where the extracted combinations does not have a combination associated with the tristimulus value Y that matches the tristimulus value Y calculated from the input image, the estimation unit 120 selects a plurality of combinations from the extracted combinations. The estimation unit 120 may select two combinations associated with two tristimulus values closest to the tristimulus value calculated from the input image. The estimation unit 120 may calculate the absolute luminance corresponding to the tristimulus value calculated from the input image by the above-described interpolation from the two absolute luminances associated with the selected two tristimulus values Y. The estimation unit 120 may select three or more combinations associated with three or more tristimulus values Y. The estimation unit 120 may derive a function as described above from the tristimulus values and the absolute luminances associated with the three or more selected combinations, for example, as described above. Then, the estimation unit 120 may calculate the absolute luminance corresponding to the tristimulus value Y calculated from the input image by the derived function.

In the case where there is no LUT brightness value that matches the target brightness value, the estimation unit 120 calculates a value p obtained by subtracting the target brightness value from the LUT brightness value. The estimation unit 120 may further calculate a value (hereinafter referred to as a corrected tristimulus value) obtained by multiplying the tristimulus value Y associated with the aperture value and the shutter speed for which the LUT brightness value is calculated by $2^p$. Then, in the case where there is a corrected tristimulus value that matches the tristimulus value calculated from the input image, the estimation unit 120 may determine the absolute luminance corresponding to the tristimulus value for which the corrected tristimulus value is calculated as the absolute luminance corresponding to the tristimulus value calculated from the input image. In the case where there is no corrected tristimulus value that matches the tristimulus value calculated from the input image, the estimation unit 120 may select two corrected tristimulus values close to the tristimulus value calculated from the input image. The estimation unit 120 may calculate the absolute luminance corresponding to the tristimulus value Y calculated from the input image by the above-described interpolation on the basis of the selected two corrected tristimulus values and two absolute luminances corresponding to the tristimulus values for which the corrected tristimulus values are calculated. The estimation unit 120 may select three or more corrected tristimulus values by a method similar to the above-described method of calculating three or more tristimulus values. Then, the estimation unit 120 may derive the absolute luminance corresponding to the tristimulus value Y calculated from the input image from the selected three or more corrected tristimulus values. The method of deriving the absolute luminance in that case may be a method similar to the above-described method of deriving the absolute luminance corresponding to the tristimulus value Y calculated from the input image on the basis of the three or more tristimulus values.

<<Relationship Storage Unit 130>>

The relationship storage unit 130 stores the relationship between the pupil size and the illuminance. The size of a human pupil (that is, pupil size) varies from about 2 mm (millimeter) to about 8 mm, depending on the illuminance of the eye part. The relationship storage unit 130 stores, for example, experimentally determined data representing the relationship between the pupil size and the illuminance. The data representing the relationship between the illuminance and the pupil, which is stored in the relationship storage unit 130, is, for example, data in which the pupil size of the case where illuminance of the eye part is the illuminance is obtained from the illuminance, or data in which the illuminance of the case where a pupil size is the pupil size is obtained from the pupil size. Hereinafter, the data indicating the relationship between the illuminance and the pupil will also be referred to as illuminance size relationship.

<<Determination Unit 140>>

The determination unit 140 receives the illuminance of the eye part from the estimation unit 120. The determination unit 140 determines the light amount of illumination to be emitted to the eye part for the pupil size to satisfy a predetermined condition (hereinafter referred to as size condition) on the basis of the illuminance of the eye part and the illuminance size relationship. The size condition may be represented by, for example, a target value of the pupil size. The size condition may be represented by a range of the pupil size. In that case, the determination unit 140 may determine the target value of the pupil size by a predetermined method on the basis of the size condition. The determination unit 140 may determine, for example, a value at the center of the range of the size represented by the size condition as the target value. The determination unit 140 may determine, for example, a largest value in the range represented by the size condition as the target value. The determination unit 140 may determine, for example, a smallest value in the range represented by the size condition as the target value. The determination unit 140 may determine another value as the target value.

The determination unit 140 determines, for example, the illuminance at which the pupil size becomes the target value (hereinafter referred to as target illuminance) on the basis of the illuminance size relationship. Then, the determination unit 140 calculates a difference between the target illuminance and received illuminance of the eye part (hereinafter also referred to as additional illuminance). The determination unit 140 determines an amount of light to be emitted to the eye part by the visible light illumination device 300 (hereinafter also referred to as the light amount of illumination) on the basis of, for example, the distance between the visible light illumination device 300 and the eye part in such a way that the illuminance of the eye part becomes the target illuminance. In other words, the determination unit 140 determines the light amount of light to be emitted by the visible light illumination device 300 on the basis of the distance between the visible light illumination device 300 and the eye part, for example in such a way that the illuminance by the visible light illumination device 300 in the eye part becomes the additional illuminance, The determination unit 140 may determine a set value of the brightness of the visible light illumination device 300, which is necessary to irradiate the eye part with the determined amount of light.

To calculate the light amount of light to be emitted by the visible light illumination device 300, the determination unit 140 may first calculate the distance from the visible light illumination device 300 to the eye part. The determination unit 140 may calculate the distance from the visible light illumination device 300 to the eye part on the basis of the imaging information of the imaging device 200 and the positional relationship between the imaging device 200 and the visible light illumination device 300, for example. Specifically, the determination unit 140 may determine the positional relationship between the imaging device 200 and the eye portion on the basis of the camera parameters of the imaging device 200, the distance from the imaging device 200 to an in-focus position, and the position of the eye region, which is the region of the eye portion in the captured image.

For example, the determination unit 140 may first calculate the direction of the eye portion with reference to the imaging device 200 on the basis of the position of the region of the eye portion on an imaged screen and the camera parameters (for example, the angle of view). In the case where the eye portion is in focus in the captured image, the eye portion is present on an in-focus surface. The shape of the in-focus surface and the position with respect to the imaging device 200 may be given to the determination unit 140 in advance. The determination unit 140 may calculate an intersection of a straight line toward the direction of the eye portion and the in-focus surface, as the position of the eye portion. The determination unit 140 may calculate a relative position of the eye portion with respect to the imaging device 200 as the position of the eye portion. The determination unit 140 may calculate the relative position of the eye portion with respect to the visible light illumination device 300 on the basis of a relative position of the eye portion with respect to the imaging device 200 and a relative position between the imaging device 200 and the visible light illumination device 300.

The determination unit 140 further calculates the light amount of the visible light illumination device 300 with which the illuminance of the position of the eye portion becomes the target illuminance on the basis of the positional relationship between the eye portion and the visible light illumination device 300 (that is, the above-described relative position), and characteristics of the illumination of the visible light illumination device 300 (for example, light distribution characteristics). The characteristics of the illumination of the visible light illumination device 300 may be the light distribution characteristics representing the light amount according to an angle from a direction that the visible light illumination device 300 faces, for example. The light distribution characteristics may be represented by, for example, a ratio to the light amount in the direction that the visible light illumination device faces. The characteristics of the illumination of the visible light illumination device 300 may be given in advance. Furthermore, the shape of the eye portion may be assumed to be a plane, for example. In other words, the shape of the eye portion may be approximated by, for example, a plane. The direction of the eye portion may be assumed to be, for example, a direction perpendicular to the direction of the walking path. For example, the estimation unit 120 may detect a face in the acquired image and estimate the direction of the detected face. In this case, the estimation unit 120 may estimate the direction of the face with reference to an orientation of the imaging device 200. The determination unit 140 may consider that the determined direction the face is a perpendicular line of a plane that approximates the eye portion. In this case, the positional relationship between the eye portion and the visible light illumination device 300 may further include the relationship between the direction of the visible light illumination device 300 and the direction of the face (for example, the angle made by the direction of the visible light illumination device 300 and the direction of the face). Then, the determination unit 140 may further calculate the light amount of the visible light illumination device 300 on the basis of the relationship between the direction of the visible light illumination device 300 and the direction of the face.

Note that, in the case where the angle of view and the focus position of the imaging device 200 are fixed, the relationship between the position on the in-focus surface and coordinates in the image captured by the imaging device 200 is fixed. In other words, the position of the eye portion with respect to the imaging device 200 can be calculated on the basis of the position of the eye portion extracted from the image acquired by the acquisition unit 110. Furthermore, the positional relationship between the imaging device 200 and the visible light illumination device 300 is also fixed. In this case, the conversion equation and the parameters for calculating the relative position with respect to the visible light illumination device 300 from the position in the image captured by the imaging device 200 may be derived in advance. Then, the determination unit 140 may calculate the relative position with respect to the visible light illumination device 300 from the position in the captured image, using the conversion equation and the parameters derived in advance and given to the determination unit 140.

The determination unit 140 may calculate a set value for the visible light illumination device 300 to emit the light of the calculated light amount on the basis of the calculated light amount, the light distribution characteristics, and the relationship between the set value of the brightness of the visible light illumination device 300 and the light amount of the light emitted by the visible light illumination device 300. The relationship between the set value of the brightness of the visible light illumination device 300 and the light amount of the light emitted by the visible light illumination device 300 may be given in advance.

The determination unit 140 sends the calculated set value to the control unit 150.

Note that the determination unit 140 may send the calculated light amount (specifically, a value representing the light amount) to the control unit 150. In that case, the control unit 150 receives the light amount from the determination unit 140. The control unit 150 may calculate a set value for the visible light illumination device 300 to emit the light of the received light amount on the basis of the received light amount, the light distribution characteristics of the visible light illumination device 300, and the relationship between the set value of the brightness of the visible light illumination device 300 and the light emitted by the visible light illumination device 300.

<<<Glare Degree>>>

The determination unit 140 may change the light amount of light to be emitted by the visible light illumination device 300 in such a way that a glare condition is satisfied. The glare condition is that glare felt by a person irradiated with light by the visible light illumination device 300 does not exceed a predetermined criterion.

Specifically, the determination unit 140 may determine the light amount of light to be emitted by the visible light illumination device 300 in such a way that the glare felt by the person irradiated with the light by the visible light illumination device 300 does not exceed the predetermined criterion. For example, a value indicating the degree of glare according to the illuminance of the eye part, in other words, an index of glare (hereinafter referred to as glare degree) may be defined. The glare degree may be, for example, an experimentally determined numerical value. In the following description, the larger the value of the glare degree, the more the glare degree indicates that the person feels too bright. In this case, the above-described predetermined criterion of the glare degree is represented by the value of the glare degree (hereinafter referred to as a glare upper limit value), which represents a limit of permissible glare. Information indicating the relationship between the illuminance of the eye part and the glare degree may be stored in the relationship storage unit 130, for example. The relationship between the illuminance of the eye part and the glare degree may be expressed in the form of a look-up table, for example. The determination unit 140 may read the relationship between the illuminance of the eye part and the glare degree from the relationship storage unit 130. The determination unit 140 can specify the illuminance of the eye part (hereinafter referred to as upper limit illuminance) corresponding to the glare upper limit value on the basis of the relationship between the illuminance of the eye part and the glare degree. The determination unit 140 may determine the additional illuminance in such a way that the glare degree does not exceed a predetermined value representing the above-described predetermined criterion (that is, the glare upper limit value) on the basis of the information indicating the relationship between the illuminance of the eye part and the glare degree.

Specifically, the determination unit 140 may calculate a maximum value (upper limit illuminance) of the illuminance of the eye part in which the glare degree does not exceed the above-described predetermined criterion (that is, the glare upper limit value) on the basis of the relationship between the illuminance of the eye part and the glare degree. The determination unit 140 may further calculate a difference between the upper limit illuminance and the illuminance of the eye part estimated by the estimation unit 120 as the maximum value of the additional illuminance. In the case where the additional illuminance calculated on the basis of the illuminance size relationship is larger than the maximum value of the additional illuminance calculated on the basis of the glare upper limit value, the determination unit 140 may change the value of the additional illuminance to the maximum value of the additional illuminance. In the case where the additional illuminance calculated on the basis of the illuminance size relationship is not larger than the maximum value of the additional illuminance calculated on the basis of the glare upper limit value, the determination unit 140 does not need to change the value of the additional illuminance.

The relationship between the illuminance and the glare degree may be determined for each type of illumination. The relationship storage unit 130 may store the relationship between the illuminance of the eye part and the glare degree for each type of illumination. The relationship storage unit 130 may individually store, for example, the relationship between the illuminance of the eye part and the glare degree by natural light (for example, light in the case where the visible light illumination device 300 does not emit light), and the relationship between the illuminance of the eye part by the visible light illumination device 300 and the glare. The glare degrees in this case may be determined in such a way that the glare degree of the case of irradiating the eye part by two light sources can be calculated on the basis of the glare degree of the case of irradiating the eye part by one of the two light sources and the glare degree of the case of irradiating the eye part by the other of the two light sources. In other words, the relationship among the glare degree of the case of irradiating the eye part by two light sources, the glare degree of the case of irradiating the eye part by one of the two light sources, and the glare degree of the case of irradiating the eye part by the other of the two light sources may be determined in advance. Hereinafter, the relationship among the glare degree of the case of irradiating the eye part by two light sources, the glare degree of the case of irradiating the eye part by one of the two light sources, and the glare degree of the case of irradiating the eye part by the other of the two light sources is referred to as a relationship among three glare degrees. The two light sources in this case are natural light and the visible light illumination device 300. The determination unit 140 may calculate a maximum value of the illuminance of the visible light illumination device 300 of the case where the visible light illumination device 300 emits light in such a way that the illuminance of the eye part satisfies the glare condition, on the basis of the estimated illuminance of the eye part and the relationship among three glare degrees.

For example, the glare degree of light to be emitted by the visible light illumination device 300 may be determined according to the illuminance by natural light. For example, the magnitude of the illuminance due to natural light may be divided into a plurality of ranges. Then, the relationship between the illuminance by the visible light illumination device 300 and the glare degree may be obtained in advance for each range of the illuminance by natural light. In this case, the determination unit 140 specifies a range including the illuminance of the eye part estimated by the estimation unit 120, and can calculate the glare degree from the illuminance by the visible light illumination device 300 on the basis of the relationship between the illuminance by the visible light illumination device 300 and the glare degree determined for the specified range. Furthermore, the determination unit 140 can calculate the illuminance by the visible light illumination device 300 of the case where the glare degree has the value from the value of the glare degree (for example, the maximum value of the glare degree that satisfies the predetermined criterion) on the basis of the relationship between the illuminance by the visible light illumination device 300 and the glare degree determined for the specified range.

The determination unit 140 calculates the maximum value of the illuminance of light by the visible light illumination device 300 of the case where the glare degree satisfies the predetermined criterion and the illuminance of the eye part in the state where the visible light illumination device 300 does not emit light is the illuminance of the eye part estimated by the estimation unit 120. The determination unit 140 may calculate the maximum value on the basis of the relationship between the illuminance by natural light and the glare degree, the relationship between the illuminance by the visible light illumination device 300 and the glare degree, and the relationship among three glare degrees. As described above, in the case where the additional illuminance calculated on the basis of the illuminance size relationship is larger than the calculated maximum value of the illuminance, the determination unit 140 may change the value of the additional illuminance to the calculated maximum value of the illuminance. In the case where the additional illuminance calculated on the basis of the illuminance size relationship is not larger than the calculated maximum value of the illuminance, the determination unit 140 does not need to change the value of the additional illuminance.

<<<Controllability>>>

The determination unit 140 determines whether the light amount of the visible light illumination device 300 can be controlled such that the pupil size satisfies the size condition. In other words, the determination unit 140 may determine whether the illuminance of the eye part can be controlled to the illuminance in which the pupil size satisfies the size condition by emission of light by the visible light illumination device 300.

Specifically, the determination unit 140 may determine whether the light amount of light that needs to be emitted by the visible light illumination device 300 in such a way as to set the illuminance of the eye part to the illuminance in which the pupil size satisfies the size condition is included in the range of the light amount of light that can be emitted by the visible light illumination device 300. Hereinafter, the light amount of light that needs to be emitted by the visible light illumination device 300 in such a way as to set the illuminance of the eye part to the illuminance in which the pupil size satisfies the size condition is referred to as a required light amount. The range of the light amount of light that can be emitted by the visible light illumination device 300 is referred to as a possible range.

In the case where the required light amount is not included in the possible range, the determination unit 140 may determine that the light amount of the visible light illumination device 300 cannot be controlled in such a way as to set the illuminance of the eye part to the illuminance in which the pupil size satisfies the size condition. In other words, in the case where the required light amount is not included in the possible range, the determination unit 140 may determine that the light amount of the visible light illumination device 300 cannot be controlled in such a way that the pupil size satisfies the size condition. In the case where the required light amount is included in the possible range, the determination unit 140 may determine that the light amount of the visible light illumination device 300 can be controlled in such a way as to set the illuminance of the eye part to the illuminance in which the pupil size satisfies the size condition. In other words, in the case where the required light amount is included in the possible range, the determination unit 140 may determine that the light amount of the visible light illumination device 300 can be controlled in such a way that the pupil size satisfies the size condition.

Specifically, in the case where the estimated illuminance of the eye part is larger than the illuminance in which the pupil size satisfies the size condition, for example, the determination unit 140 may determine that the illuminance of the eye part cannot be controlled to the illuminance in which the pupil size satisfies the size condition by emission of light by the visible light illumination device 300. In the case where the illuminance of the eye part irradiated with light of the maximum light amount is smaller than the illuminance in which the pupil size satisfies the size condition, for example, the determination unit 140 may determine that the illuminance of the eye part cannot be controlled to the illuminance in which the pupil size satisfies the size condition by emission of light by the visible light illumination device 300. Note that the above-described maximum light amount is the light amount of the strongest light that can be emitted by the visible light illumination device 300.

In the case of determining that the illuminance of the eye part cannot be controlled to the illuminance in which the pupil size satisfies the size condition, the determination unit 140 may send a notification indicating that the illuminance of the eye part cannot be controlled to the illuminance in which the pupil size satisfies the size condition by the visible light illumination device 300 via the notification unit 160. Hereinafter, the notification indicating that the illuminance of the eye part cannot be controlled to the illuminance in which the pupil size satisfies the size condition by the visible light illumination device 300 is referred to as an uncontrollable notification. The determination unit 140 may send an instruction to transmit the uncontrollable notification to the notification unit 160, for example. As will be described below, when receiving the instruction to transmit the uncontrollable notification, the notification unit 160 sends the uncontrollable notification to a predetermined notification destination (for example, the notification destination device 500).

<<<Glare Degree and Controllability>>>

Note that the determination unit 140 may be set to make a determination that the illuminance of the eye part cannot be controlled to the illuminance in which the pupil size satisfies the size condition in the case where the additional illuminance calculated on the basis of the illuminance size relationship is larger than the maximum value of the illuminance in such a way as to satisfy the glare condition. In this case, the determination unit 140 may send the instruction to transmit the uncontrollable notification to the notification unit 160.

The determination unit 140 may determine whether the illuminance of the eye part can be controlled to the illuminance in which the pupil size satisfies the size condition by emission of light by the visible light illumination device 300 regardless of whether the glare condition is satisfied. Then, in the case where the determination unit 140 determines that the light amount of the visible light illumination device 300 cannot be controlled such that the pupil size satisfies the size condition, the determination unit 140 may send the instruction to transmit the uncontrollable notification to the notification unit 160. Moreover, the determination unit 140 may determine whether the additional illuminance calculated on the basis of the illuminance size relationship is larger than the maximum value of the illuminance in such a way as to satisfy the glare condition. In the case where the additional illuminance calculated on the basis of the illuminance size relationship is larger than the calculated maximum value of the illuminance, the determination unit 140 may change the value of the additional illuminance to the calculated maximum value of the illuminance. Moreover, the determination unit 140 may send an instruction to transmit a notification indicating that the glare condition is not satisfied to the notification unit 160 in the case where the additional illuminance calculated on the basis of the illuminance size relationship is larger than the maximum value of the illuminance in such a way as to satisfy the glare condition.

Note that the determination unit 140 may determine that the illuminance of the eye part can be controlled to the illuminance in which the pupil size satisfies the size condition in the case where the additional illuminance calculated on the basis of the illuminance size relationship is smaller than the maximum value of the illuminance in such a way as to satisfy the glare condition.

Note that, in the following description of operation, the determination unit 140 determines whether the illuminance of the eye part can be controlled to the illuminance in which the pupil size satisfies the size condition by emission of light by the visible light illumination device 300 regardless of whether the glare condition is satisfied. Furthermore, in the case where the additional illuminance calculated on the basis of the illuminance size relationship is larger than the maximum value of the illuminance in such a way as to satisfy the glare condition, the determination unit 140 does not send the instruction to transmit the notification indicating that the glare condition is not satisfied.

<<Control unit 150>>

The control unit 150 controls the visible light illumination device 300 in such a way that the visible light illumination device 300 emits the light of the light amount determined by the determination unit 140.

Specifically, the control unit 150 receives, from the control unit 150, the set value of the visible light illumination device 300 for the visible light illumination device 300 to emit the light of the light amount determined by the determination unit 140. The control unit 150 sets the received set value in the visible light illumination device 300.

After setting the received set value in the visible light illumination device 300, the control unit 150 may transmit an instruction to perform imaging to the imaging device 200. In the case where the imaging device 200 is set to continue imaging, the control unit 150 does not have to send the instruction to perform imaging to the imaging device 200.

Note that, as described above, the determination unit 140 may send the calculated light amount (specifically, a value representing the light amount) to the control unit 150. In that case, the control unit 150 receives the light amount from the determination unit 140. The control unit 150 may calculate a set value for the visible light illumination device 300 to emit the light of the received light amount on the basis of the received light amount, the light distribution characteristics of the visible light illumination device 300, and the relationship between the set value of the brightness of the visible light illumination device 300 and the light emitted by the visible light illumination device 300.

<<Notification Unit 160>>

In the case where the determination unit 140 sends an unsettable notification, the notification unit 160 receives an instruction to transmit the unsettable notification from the determination unit 140. As described below, when receiving the unsettable notification, the notification unit 160 transmits the unsettable notification to a predetermined notification destination (for example, the notification destination device 500). The unsettable notification may be a predetermined signal or the like. The unsettable notification may indicate a reason why the illuminance of the eye part cannot be controlled to the target illuminance. The reason why the illuminance of the eye part cannot be controlled to the target illuminance is that, for example, the illuminance of the eye part by natural light is too bright, or the illuminance of the eye part by natural light is too dark.

The notification unit 160 may receive the instruction to transmit the notification indicating that the glare condition cannot be satisfied (hereinafter referred to as a glare notification) from the determination unit 140. When receiving the instruction to transmit the glare notification, the notification unit 160 transmits the glare notification to a predetermined notification destination. The glare notification may be a predetermined signal or the like different from the unsettable notification.

<<Image Storage Unit 170>>

The image storage unit 170 stores the image and the imaging information acquired by the acquisition unit 110. For example, in the case where the light amount of light emitted by the visible light illumination device 300 is controlled by the control unit 150, and the pupil size of the eye part is changed to satisfy the size condition, the pupil size satisfies the size condition in the image newly acquired by the acquisition unit 110 and to be stored in the image storage unit 170.

<<Notification Destination Device 500>>

The notification destination device 500 receives the unsettable notification transmitted by the notification unit 160. The notification destination device 500 performs output according to the received unsettable notification. The notification destination device 500 may be, for example, a terminal device held by the administrator of the imaging system 1. The notification destination device 500 may be, for example, a display device that displays information output from the control device 100. The notification destination device 500 may display, as the output according to the unsettable notification, a display (for example, a message) indicating that the illuminance of the eye part cannot be set to the illuminance in which the pupil size satisfies the size condition by the visible light illumination device 300, for example. The notification destination device 500 may output, for example, a predetermined sound as the output according to the unsettable notification. The notification destination device 500 may output, for example, a predetermined image or animation as the output according to the unsettable notification. The notification destination device 500 may vibrate in a predetermined pattern, for example, as the output according to the unsettable notification. The notification destination device 500 may output a combination of two or more of the above examples as the output according to the unsettable notification.

The notification destination device 500 may further receive the glare notification transmitted by the notification unit 160. The notification destination device 500 performs output according to the received glare notification.

<<Operation>>

Next, an operation of the control device 100 according to the present example embodiment will be described in detail with reference to the drawings.

Figure 3:
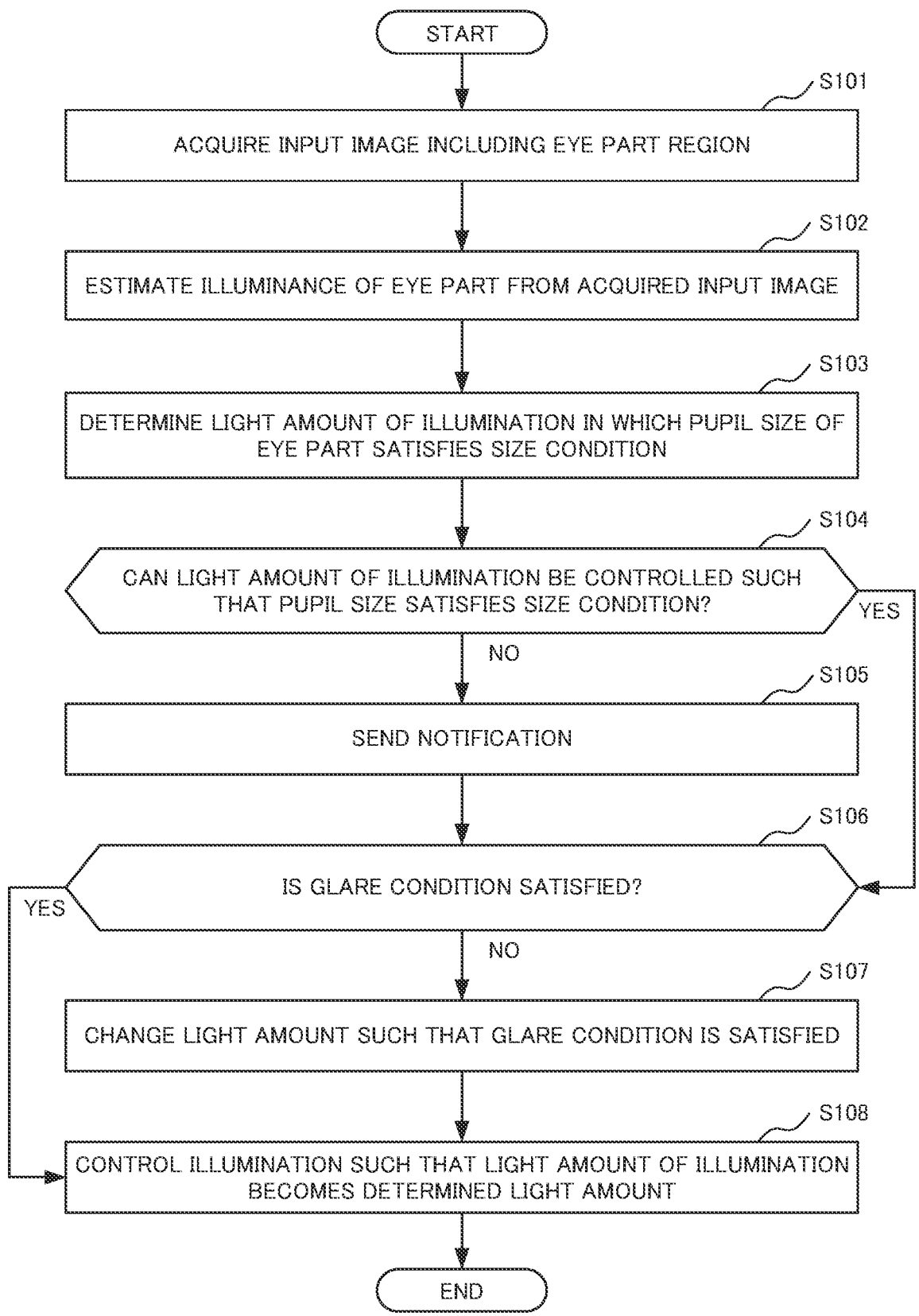
FIG. 3 is a flowchart illustrating an example of an operation of the imaging system according to the first example embodiment of the present disclosure.

FIG. 3 is a flowchart illustrating an example of an operation of the control device 100 according to the present example embodiment. In the operation illustrated in FIG. 3, the acquisition unit 110 acquires an input image of a region of an eye part (step S101). Next, the estimation unit 120 estimates the illuminance of the eye part from the acquired input image. In the present example embodiment, the estimation unit 120 estimates the illuminance of the eye part on the basis of the pixel value of the sclera region in the eye region of the acquired input image.

Next, the determination unit 140 determines the light amount of the illumination in which the pupil size of the eye part satisfies the size condition. The determination unit 140 determines whether the light amount of the illumination can be controlled such that the pupil size satisfies the size condition (step S104). In the case where the light amount of the illumination cannot be controlled such that the pupil size satisfies the size condition (NO in step S104), the control device 100 sends a notification to the notification destination device 500, for example. Specifically, the determination unit 140 sends the instruction to transmit the unsettable notification to the notification unit 160. When receiving the instruction to transmit the unsettable notification, the notification unit 160 transmits the unsettable notification to the notification destination device 500. The control device 100 then performs the operation of step S106.

In the case where the light amount of the illumination can be controlled such that the pupil size satisfies the size condition (YES in step S104), the control device 100 then performs the operation of step S106.

In step S106, the determination unit 140 determines whether the glare condition is satisfied in the case where the visible light illumination device 300 emits the light of the light amount determined in step S103. In the case where the glare condition is satisfied (YES in step S106), the control device 100 then performs the operation of step S108.

In the case where the glare condition is not satisfied (NO in step S106), the determination unit 140 changes the light amount of light emitted by the visible light illumination device 300 in such a way as to satisfy the glare condition (step S107). The control device 100 then performs the operation of step S108.

In step S108, the control unit 150 controls the light amount of the visible light illumination device 300 in such a way that the light amount of the visible light illumination device 300 becomes the determined light amount. Specifically, the determination unit 140 may determine the set value of the visible light illumination device 300 for setting the light amount of the visible light illumination device 300 to the determined light amount on the basis of the relationship between the set value and the light amount represented by a look-up table, for example. The determination unit 140 transmits the determined set value to the control unit 150. The control unit 150 receives the set value from the determination unit, and sets the set value of the visible light illumination device 300 to the received set value.

<<Effect>>

The present example embodiment has an effect of shortening the time required to obtain an iris image in a desired state. The iris image in a desired state is, for example, an iris image having the pupil size that satisfies the size condition. The reason is that the estimation unit 120 estimates the illuminance of the eye part from the acquired input image, and the determination unit 140 determines the light amount of light to be emitted by the visible light illumination device 300 in such a way that the pupil size of the eye part satisfies the size condition. The control unit 150 controls the visible light illumination device 300 in such a way that the light amount to be emitted by the visible light illumination device 300 becomes the determined light amount, in such a way that the pupil size changes in such a way that the pupil size of the eye part satisfies the size condition. By imaging the eye part after the pupil size has changed, the iris image in a desired state can be obtained.

<First Modification>

Next, a first modification will be described. First to fifth modifications to be described below represent examples of modifications of the first example embodiment.

<<Configuration>>

The imaging system 1 of the present modification is the same as the imaging system of the first example embodiment except for differences in the control device 100 to be described below. The control device 100 of the present modification is the same as the control device 100 of the first example embodiment except for the following differences.

In the first modification, the estimation unit 120 detects the iris region in the input image, and further estimates an iris color on the basis of the pixel values of the pixels included in the detected iris region. The estimation unit 120 may estimate which of a plurality of predefined colors the iris color is, on the basis of the pixel values of the pixels in the detected iris region. The estimation unit 120 sends information representing the estimated iris color to the determination unit 140.

The relationship storage unit 130 stores an illuminance size relationship for each iris color. The relationship storage unit 130 may store, for example, a look-up table representing the relationship between the illuminance of the eye part and the pupil size as the illuminance size relationship for each of a plurality of predefined colors.

The determination unit 140 receives the information representing the estimated iris color from the estimation unit 120. The determination unit 140 reads the illuminance size relationship stored for the estimated iris color, and determines the light amount of light to be emitted by the visible light illumination device 300 on the basis of the read illuminance size relationship.

In the present modification, a glare condition is further obtained for each iris color. For example, the glare condition set for each iris color may be stored in the relationship storage unit 130.

The determination unit 140 may read the glare condition for the estimated iris color from, for example, the relationship storage unit 130. The determination unit 140 may store the glare condition for each iris color and select the glare condition for the estimated iris color. The determination unit 140 may change the light amount of light to be emitted by the visible light illumination device 300 or send the instruction to transmit the glare notification according to the above-described glare degree on the basis of the glare condition for the estimated iris color.

The same glare condition may be defined for each of a plurality of iris colors. Then, the relationship between the illuminance and the glare degree may be defined for each iris color. In that case, the relationship storage unit 130 may store the relationship between the illuminance and the glare degree for each iris color. The determination unit 140 may determine the glare degree from the illuminance, using the relationship between the illuminance and the glare degree for each iris color. Furthermore, the determination unit 140 may determine the illuminance in which the glare degree becomes the value from the value of the glare degree, using the relationship between the illuminance and the glare degree for each iris color.

<<Operation>>

Next, an operation of the control device 100 of the present modification will be described in detail with reference to the drawings.

Figure 4:
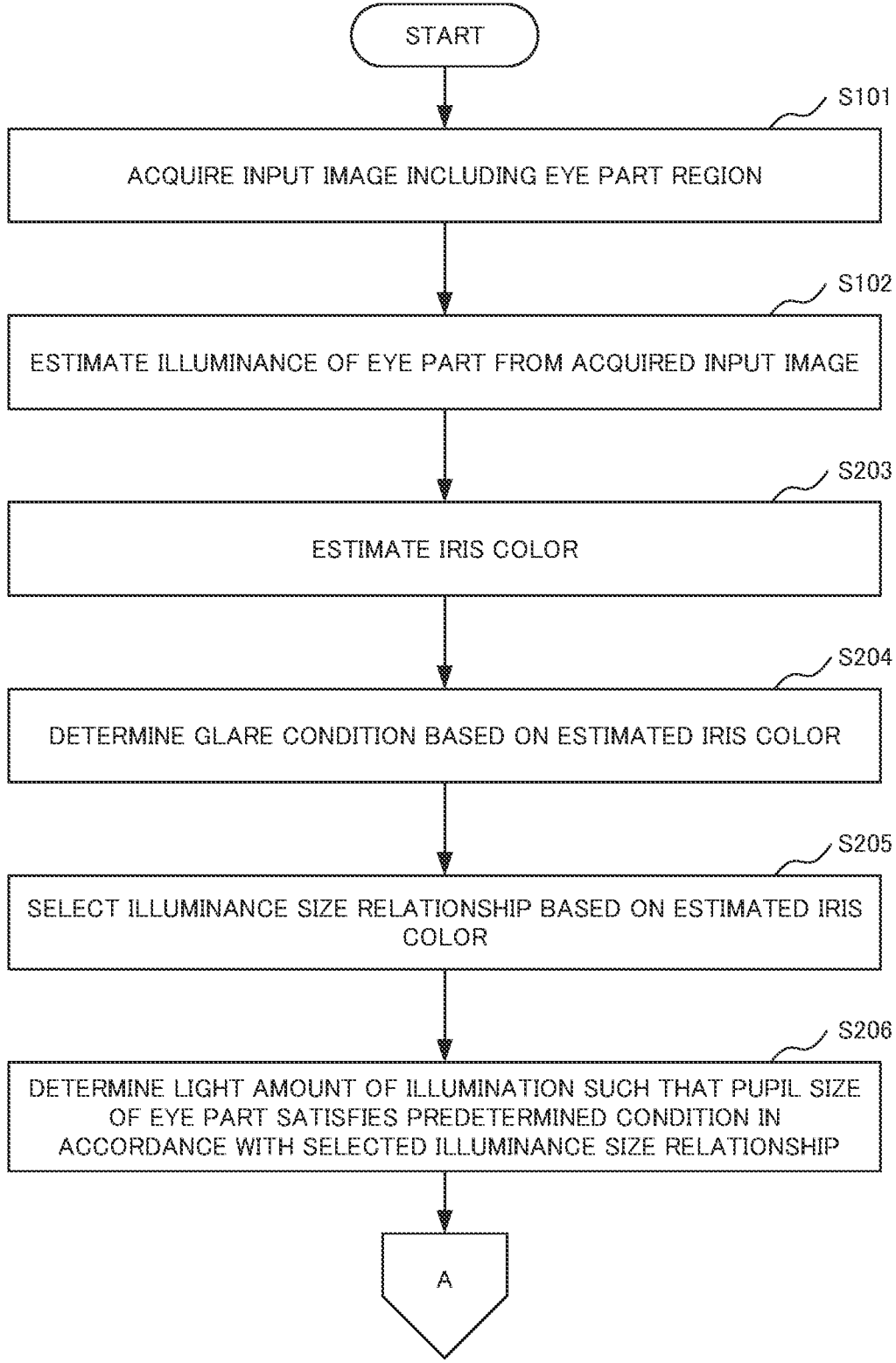
FIG. 4 is a flowchart illustrating an example of an operation of a control device according to a first modification of the first example embodiment of the present disclosure.
Figure 5:
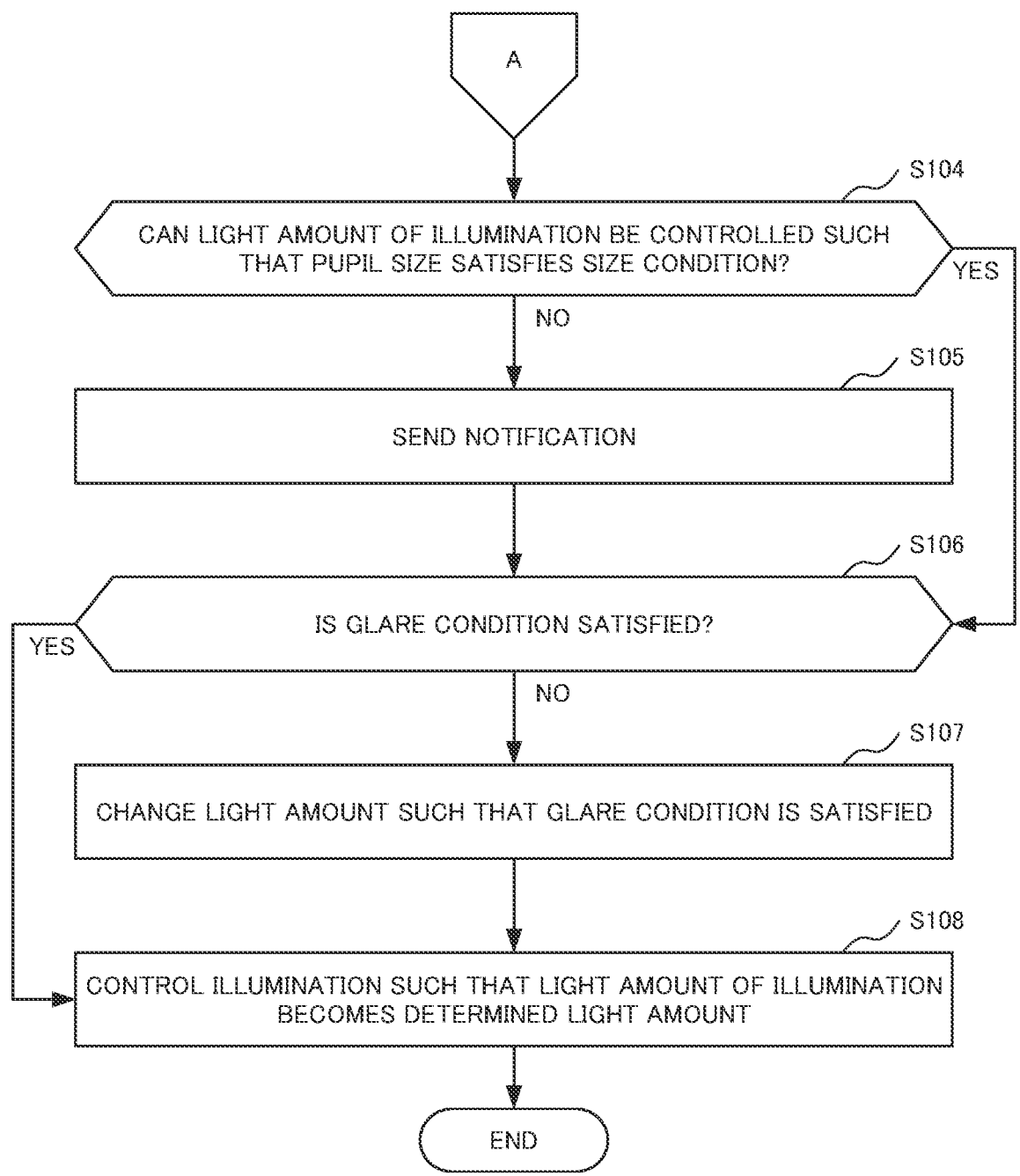
FIG. 5 is a flowchart illustrating an example of the operation of the control device according to the first modification of the first example embodiment of the present disclosure.

FIGS. 4 and 5 are flowcharts illustrating an example of an operation of the control device 100 according to the present modification.

In steps S101 and S102 illustrated in FIG. 4, the control device 100 performs the same operation as the operation of steps S101 and S102 of the control device 100 of the first example embodiment illustrated in FIG. 3.

In step S203, the estimation unit 120 estimates the iris color on the basis of the input image (step S203). The estimation unit 120 may detect the iris region from the input image, for example. The estimation unit 120 may estimate the iris color from the pixel values of the pixels included in the iris region. The estimation unit 120 may estimate, for example, a color corresponding to the iris color in the detected region from a plurality of predetermined iris colors. The estimation unit 120 sends the information representing the estimated iris color to the determination unit 140. The determination unit 140 receives the information representing the iris color from the estimation unit 120.

Next, the determination unit 140 determines the glare condition on the basis of the estimated iris color (step S204). The determination unit 140 may select the glare condition defined for the estimated iris color from a plurality of glare conditions.

Next, the determination unit 140 selects the illuminance size relationship on the basis of the estimated iris color (step S205). The determination unit 140 may select the illuminance size relationship defined for the estimated iris color from a plurality of illuminance size relationships.

The determination unit 140 determines the light amount of illumination (that is, the light amount of light to be emitted by the visible light illumination device 300) in which the pupil size of the eye part satisfies a predetermined condition (that is, the above-described size condition) on the basis of the selected illuminance size relationship (step S206). Next, the control device 100 performs the operation of step S104 of FIG. 5.

The operation from step S104 to step S108 of the control device 100 of the present modification illustrated in FIG. 5 is the same as the operation from step S104 to step S108 of the control device 100 of the first example embodiment illustrated in FIG. 3.

Note that, as described above, the determination unit 140 may control the visible light illumination device 300 in such a way that the illuminance of the eye part becomes the illuminance in which the glare degree satisfies the glare condition on the basis of the relationship between the illuminance and the glare degree according to the iris color, using the same glare condition regardless of the iris color. In that case, the determination unit 140 selects the relationship between the illuminance and the glare degree defined for the estimated iris color in step S204. Other operations are the same as the operation examples described above.

<<Effect>>

The present modification has the same effect as the first example embodiment. The reason is the same as the reason why the effect of the first example embodiment is exhibited.

The present modification further has a second effect of obtaining an iris image in a desired state regardless of the iris color. The reason is that the estimation unit 120 estimates the iris color from the input image, and the determination unit 140 determines the light amount of light to be emitted by the visible light illumination device 300 on the basis of the illuminance size relationship according to the estimated iris color.

This present modification further has a third effect of appropriately reducing the glare regardless of the iris color. The reason is that the determination unit 140 changes the light amount of light to be emitted by the visible light illumination device 300 on the basis of the glare condition according to the estimated iris color.

Note that, in the present modification, the determination unit 140 may change the light amount of light to be emitted by the visible light illumination device 300 on the basis of the same glare condition regardless of the iris color. In that case, the same effect as that of the first example embodiment and the above-described second effect can be obtained by the present modification.

Furthermore, in the present modification, the determination unit 140 may determine the light amount of light to be emitted by the visible light illumination device 300 on the basis of the same illuminance size relationship regardless of the iris color. In that case, the same effect as that of the first example embodiment and the above-described third effect can be obtained by the present modification.

<Second Modification>

Next, a second modification will be described. An imaging system 1A of the present modification is the same as the imaging system 1 of the first example embodiment except for differences to be described below.

<<Configuration>>

Figure 6:
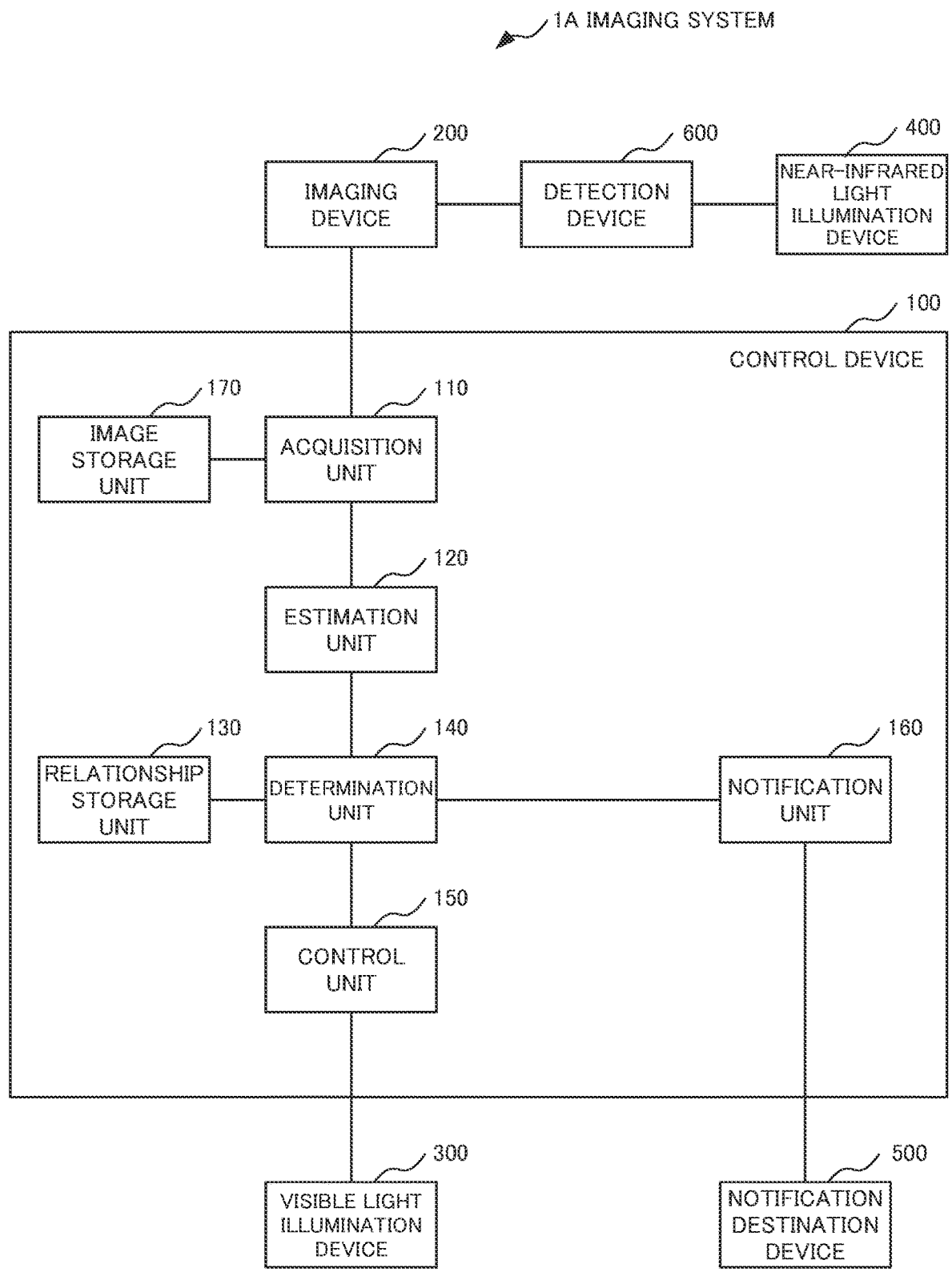
FIG. 6 is a block diagram illustrating an example of a configuration of an imaging system according to a second modification of the first example embodiment of the present disclosure.

FIG. 6 is a block diagram illustrating an example of a configuration of the imaging system 1A according to the present modification. The imaging system 1A of the present modification includes a detection device 600 in addition to the control device 100, the imaging device 200, the visible light illumination device 300, the near-infrared light illumination device 400, the notification destination device 500.

The detection device 600 detects a person, for example, in the above-described walking path. In the case where a person starts to be detected, the detection device 600 transmits a notification indicating that the person has started to be detected to the imaging device 200 and the near-infrared light illumination device 400. In the case where the person is no longer detected, the detection device 600 transmits a notification indicating that the person is no longer detected to the imaging device 200 and the near-infrared light illumination device 400. The notification indicating that the person has started to be detected (hereinafter referred to as detection notification) may be implemented by transmitting a predetermined signal (hereinafter also referred to as detection signal). The notification indicating that the person is no longer detected (hereinafter, non-detection notification) may be implemented by transmitting another predetermined signal (non-detection signal). The detection notification may be implemented by starting the transmission of the predetermined signal (hereinafter referred to as detection continuation signal). The non-detection notification may be implemented by termination of the transmission of the detection continuation signal. The detection device 600 may be implemented by a sensor that detects a person or the like by, for example, near-infrared light or ultrasonic waves.

The imaging device 200 receives the detection notification and the non-detection notification from the detection device 600. The imaging device 200 continuously performs imaging during a period from reception of the detection notification to reception of the non-detection notification from the detection device 600, and transmits an image obtained by the imaging to the control device 100. In the case of receiving the non-detection notification, the imaging device 200 may suspend the imaging and the transmission of the image until receiving the next detection notification.

The near-infrared light illumination device 400 receives the detection notification and the non-detection notification from the detection device 600. The near-infrared light illumination device 400 continuously emits near-infrared light during a period from reception of the detection notification to reception of the non-detection notification from the detection device 600. In the case of receiving the non-detection notification, the near-infrared light illumination device 400 may suspend the irradiation of the near-infrared light until receiving the next detection notification.

<<Operation>>

The control device 100 of the present modification performs the same operation as that of the first example embodiment.

<Third Modification>

Next, a third modification will be described. An imaging system 1B of the present modification is the same as the imaging system 1A of the second modification except for differences to be described below.

<<Configuration>>

Figure 7:
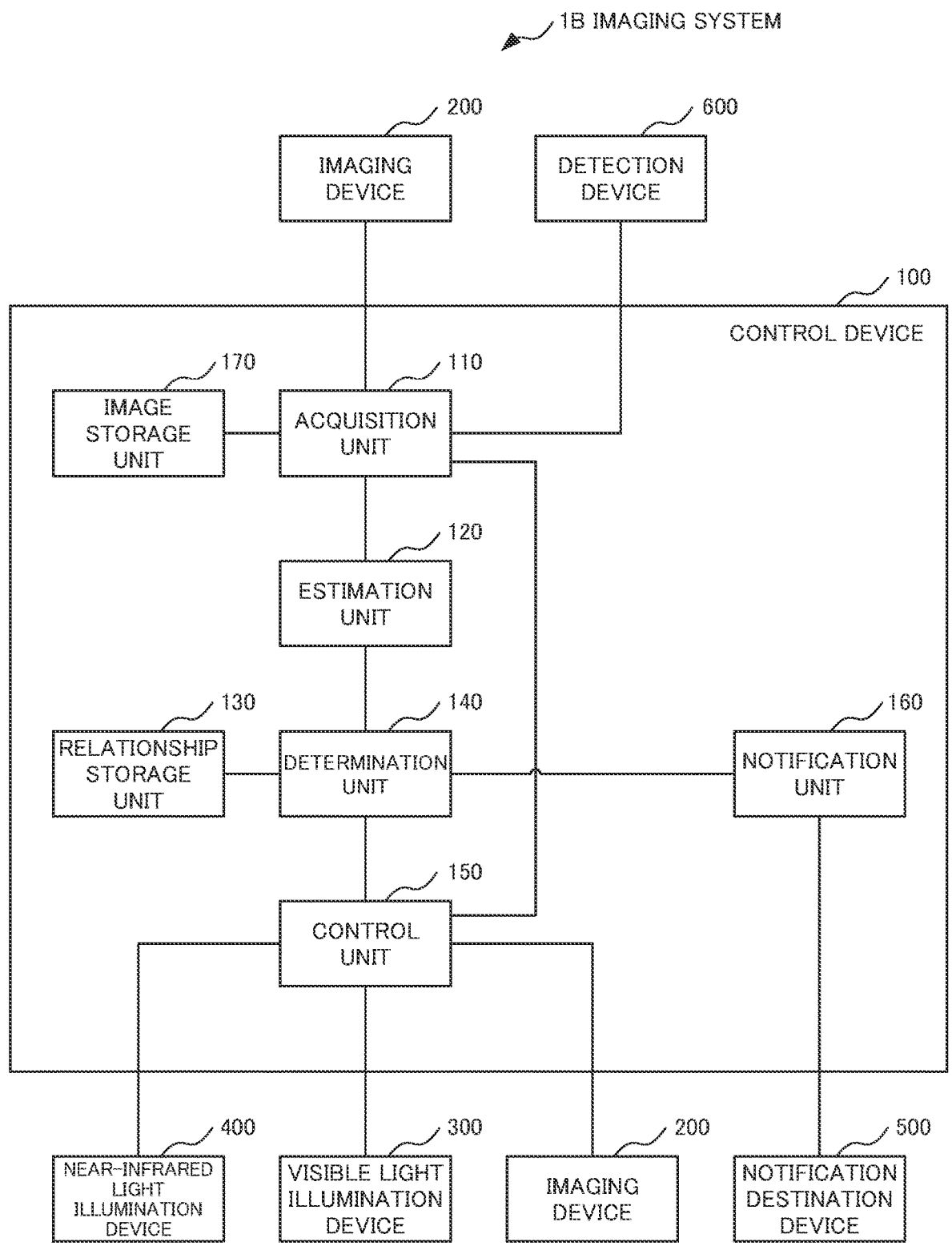
FIG. 7 is a block diagram illustrating an example of a configuration of an imaging system according to a third modification of the first example embodiment of the present disclosure.

FIG. 7 is a block diagram illustrating an example of a configuration of the imaging system 1B according to the present modification. The imaging system 1B of the present modification includes the detection device 600 in addition to the control device 100, the imaging devices 200, the visible light illumination device 300, the near-infrared light illumination device 400, the notification destination device 500, similarly to the imaging system 1A of the first modification. FIG. 7 illustrates two imaging devices 200. Note that the imaging device 200 illustrated above the control device 100 is the same imaging device 200 as the imaging device 200 illustrated below the control device 100. In other words, the same imaging devices 200 are illustrated above the control device 100 and below the control device 100. In the present modification, the imaging devices 200 are respectively connected to the acquisition unit 110 and the control unit 150 of the control device 100. The near-infrared light illumination device 400 is connected to the control unit 150 of the control device 100. The detection device 600 is connected to the acquisition unit 110 of the control device 100.

The detection device 600 detects a person, for example, in the above-described walking path. In the present modification, the detection device 600 transmits the detection notification and the non-detection notification to the acquisition unit 110 of the control device 100.

The acquisition unit 110 receives the detection notification and the non-detection notification from the detection device 600. In the case of receiving the detection notification from the detection device 600, the acquisition unit 110 sends, to the control unit 150, an instruction to transmit the detection notification to the imaging device 200 and the near-infrared light illumination device 400. In the case of receiving the non-detection notification from the detection device 600, the acquisition unit 110 sends, to the control unit 150, an instruction to transmit the non-detection notification to the imaging device 200 and the near-infrared light illumination device 400.

The control unit 150 receives the instruction to transmit the detection notification and the instruction to transmit the non-detection notification from the acquisition unit 110. In the case of receiving the instruction to transmit the detection notification from the acquisition unit 110, the control unit 150 transmits the detection notification to the imaging device 200 and the near-infrared light illumination device 400. In the case of receiving the instruction to transmit the non-detection notification from the acquisition unit 110, the control unit 150 transmits the non-detection notification to the imaging device 200 and the near-infrared light illumination device 400.

The imaging device 200 receives the detection notification and the non-detection notification from the control unit 150. The imaging device 200 continuously performs imaging during a period from reception of the detection notification to reception of the non-detection notification from the control unit 150, and transmits an image obtained by the imaging to the control device 100. In the case of receiving the non-detection notification, the imaging device 200 may suspend the imaging and the transmission of the image until receiving the next detection notification.

The near-infrared light illumination device 400 receives the detection notification and the non-detection notification from the control unit 150. The near-infrared light illumination device 400 continuously emits near-infrared light during a period from the reception of the detection notification to the reception of the non-detection notification from the control unit 150. In the case of receiving the non-detection notification, the near-infrared light illumination device 400 may suspend the irradiation of the near-infrared light until receiving the next detection notification.

<<Operation>>

The control device 100 of the present modification performs the same operation as that of the first example embodiment.

<Fourth Modification>

Next, a fourth modification will be described. An imaging system 1C of the present modification is the same as the imaging system 1 of the first example embodiment except for differences to be described below.

<<Configuration>>

Figure 8:
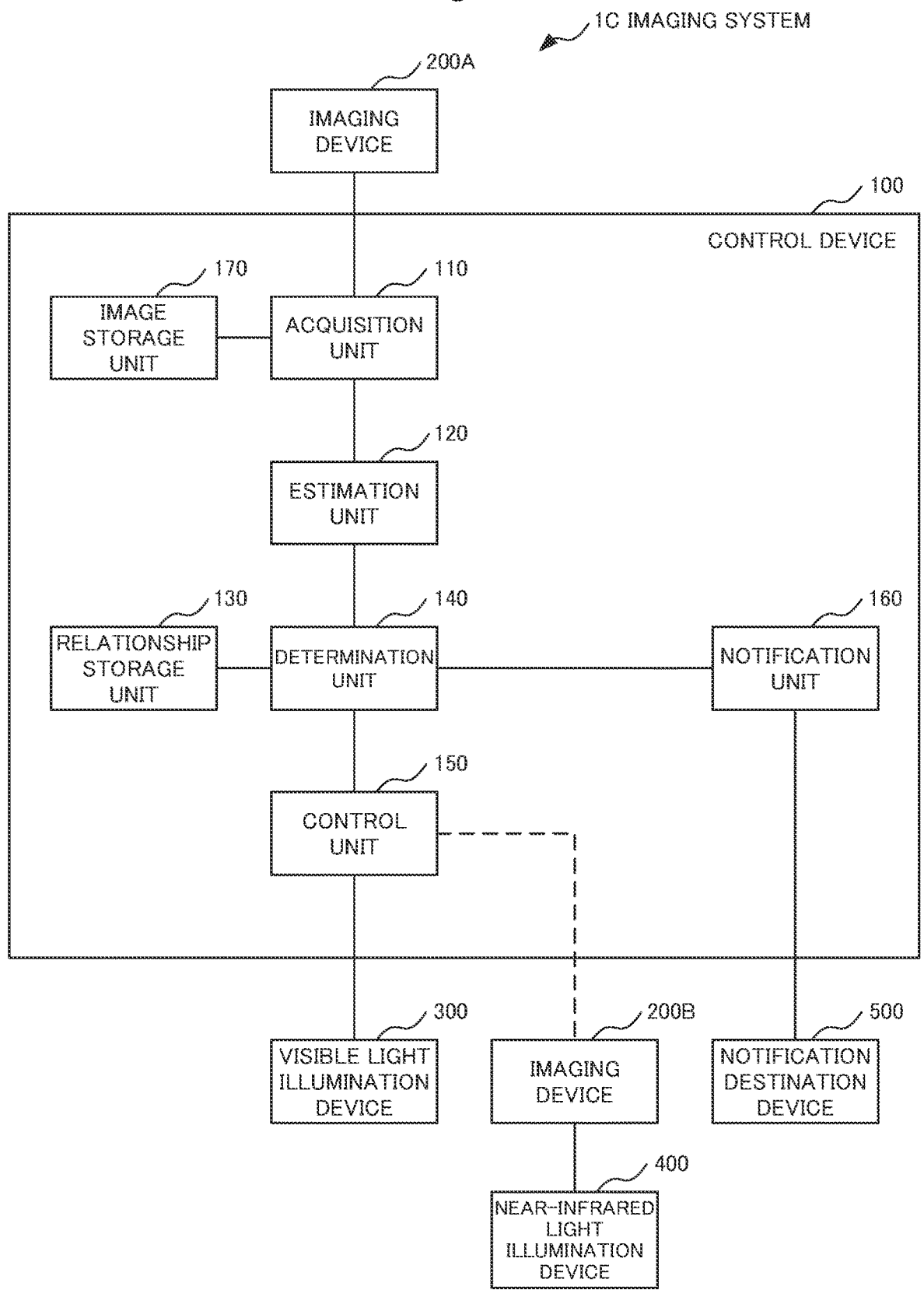
FIG. 8 is a block diagram illustrating a configuration of an imaging system according to a fourth modification of the first example embodiment of the present disclosure.

FIG. 8 is a block diagram illustrating a configuration of the imaging system 1C of the present modification. The imaging system 1C of FIG. 8 includes an imaging device 200A and an imaging device 200B instead of the imaging device 200. In the example illustrated in FIG. 8, the near-infrared light illumination device 400 is connected to the imaging device 200B.

The imaging device 200A and the imaging device 200B are attached in such a way as to be able to image the head of a person walking along the above-described walking path, for example. The focus position of the imaging device 200A and the focus position of the imaging device 200B are fixed. The focus position of the imaging device 200A and the focus position of the imaging device 200B are set such that the head of a person walking along the walking path passes through the focus position of the imaging device 200A and then passes through the focus position of the imaging device 200B. The imaging device 200A and the imaging device 200B may continuously perform imaging. The near-infrared light illumination device 400 may continuously emit near-infrared light.

The control unit 150 may control the visible light illumination device 300 in such a way that the light amount of light emitted by the visible light illumination device 300 becomes the determined light amount, and then transmit an instruction to the imaging device 200B to perform imaging. In this case, the imaging device 200B may start imaging according to the instruction from the control unit 150. The imaging device 200B may transmit a notification to start imaging to the near-infrared light illumination device 400 before starting imaging. The imaging device 200B may transmit a notification to terminate imaging to the near-infrared light illumination device 400 before terminating imaging. The near-infrared light illumination device 400 may receive the notification to start imaging and the notification to terminate imaging from the imaging device 200B. The near-infrared light illumination device 400 may continue to emit near-infrared light while the imaging device 200B is performing imaging, for example, in a period from reception of the notification to start imaging to reception of the notification to terminate imaging.

The acquisition unit 110 of the present modification receives the image captured by the imaging device 200A.

<<Operation>>

The control device 100 of the present modification performs the same operation as the control device 100 of the first example embodiment illustrated in FIG. 3.

Note that the control unit 150 of the present example embodiment may transmit an instruction to perform imaging to the imaging device 200B after controlling the illumination in step S108, that is, after setting the set value of brightness of the visible light illumination device 300. In this case, the imaging device 200B may start imaging when receiving the instruction to perform imaging. When receiving the instruction to perform imaging, the imaging device 200B may perform imaging.

<Fifth Modification>

Next, a fifth modification of the present modification will be described.

At least two of the first modification, the second modification or the third modification, and the fourth modification may be combined. The fifth modification is a combination of at least two of the first modification, the second modification or the third modification, and the fourth modification.

In the case of combining the first modification, and the second modification or the third modification, the imaging device 200 does not have to be connected to the near-infrared light illumination device 400. In the case of combining the first modification and the fourth modification, the imaging device 200 does not have to be connected to the near-infrared light illumination device 400. In the case of combining only the first modification and the fourth modification, the configuration of the imaging system of the fifth modification may be the same as the configuration of the imaging system 1C of the fourth modification illustrated in FIG. 8.

In the case of combining the first modification and the second modification, the detection device 600 is connected to the imaging device 200 and the near-infrared light illumination device 400, as in the example illustrated in FIG. 6. Then, the detection notification and the non-detection notification are transmitted from the detection device 600 to the imaging device 200 and the near-infrared light illumination device 400. In the case of combining the first modification and the third modification, the control unit 150 is connected to the imaging device 200 and the near-infrared light illumination device 400, as in the example illustrated in FIG. 7. Then, the detection notification and the non-detection notification are transmitted from the control unit 150 to the imaging device 200 and the near-infrared light illumination device 400.

In the case of combining the second modification or the third modification, and the fourth modification, the imaging device 200B does not have to be connected to the near-infrared light illumination device 400. The same similarly applies to the case of combining the first modification, the second modification or the third modification, and the fourth modification.

In the case of combining the second modification and the fourth modification, the detection device 600 is connected to the imaging device 200A, the imaging device 200B, and the near-infrared light illumination device 400. Then, the detection notification and the non-detection notification are transmitted from the detection device 600 to the imaging device 200A, the imaging device 200B, and the near-infrared light illumination device 400. The imaging device 200A and the imaging device 200B may continuously perform imaging during a period from reception of the detection notification to reception of the non-detection notification. The near-infrared light illumination device 400 may continuously emit near-infrared light during a period from reception of the detection notification to reception of the non-detection notification. The same similarly applies to the case of combining the first modification, the second modification, and the fourth modification.

In the case of combining the third modification and the fourth modification, the control unit 150 may be connected to the imaging device 200A, the imaging device 200B, and the near-infrared light illumination device 400. Then, the detection notification and the non-detection notification may be transmitted from the control unit 150 to the imaging device 200A, the imaging device 200B, and the near-infrared light illumination device 400. Then, the detection notification and the non-detection notification are transmitted from the detection device 600 to the imaging device 200A, the imaging device 200B, and the near-infrared light illumination device 400. The imaging device 200A and the imaging device 200B may continuously perform imaging during a period from reception of the detection notification to reception of the non-detection notification. The near-infrared light illumination device 400 may continuously emit near-infrared light during a period from reception of the detection notification to reception of the non-detection notification. The same similarly applies to the case of combining the first modification, the third modification, and the fourth modification.

In the case of combining the second modification and the fourth modification, the detection device 600 may be connected to the imaging device 200A. Then, the detection notification and the non-detection notification may be transmitted from the detection device 600 to the imaging device 200A. The imaging device 200A may continuously perform imaging during a period from reception of the detection notification to reception of the non-detection notification. In this case, the imaging device 200B may continuously perform imaging, and the near-infrared light illumination device 400 may continuously emit near-infrared light. Furthermore, in this case, the control unit 150 may transmit the instruction to start imaging to the imaging device 200B. The imaging device 200B may start imaging according to the instruction from the control unit 150. Moreover, the imaging device 200B may transmit the notification to the near-infrared light illumination device 400 when starting imaging. When receiving the notification, the near-infrared light illumination device 400 may start emission of near-infrared light. The same similarly applies to the case of combining the first modification, the second modification, and the fourth modification.

Second Example Embodiment

Next, a second example embodiment of the present disclosure will be described in detail with reference to the drawings. In the present example embodiment, a pupil size of a captured eye portion is estimated from an image captured by an imaging device 200, and illuminance of the eye portion is estimated on the basis of the pupil size.

<<Configuration>>

Figure 9:
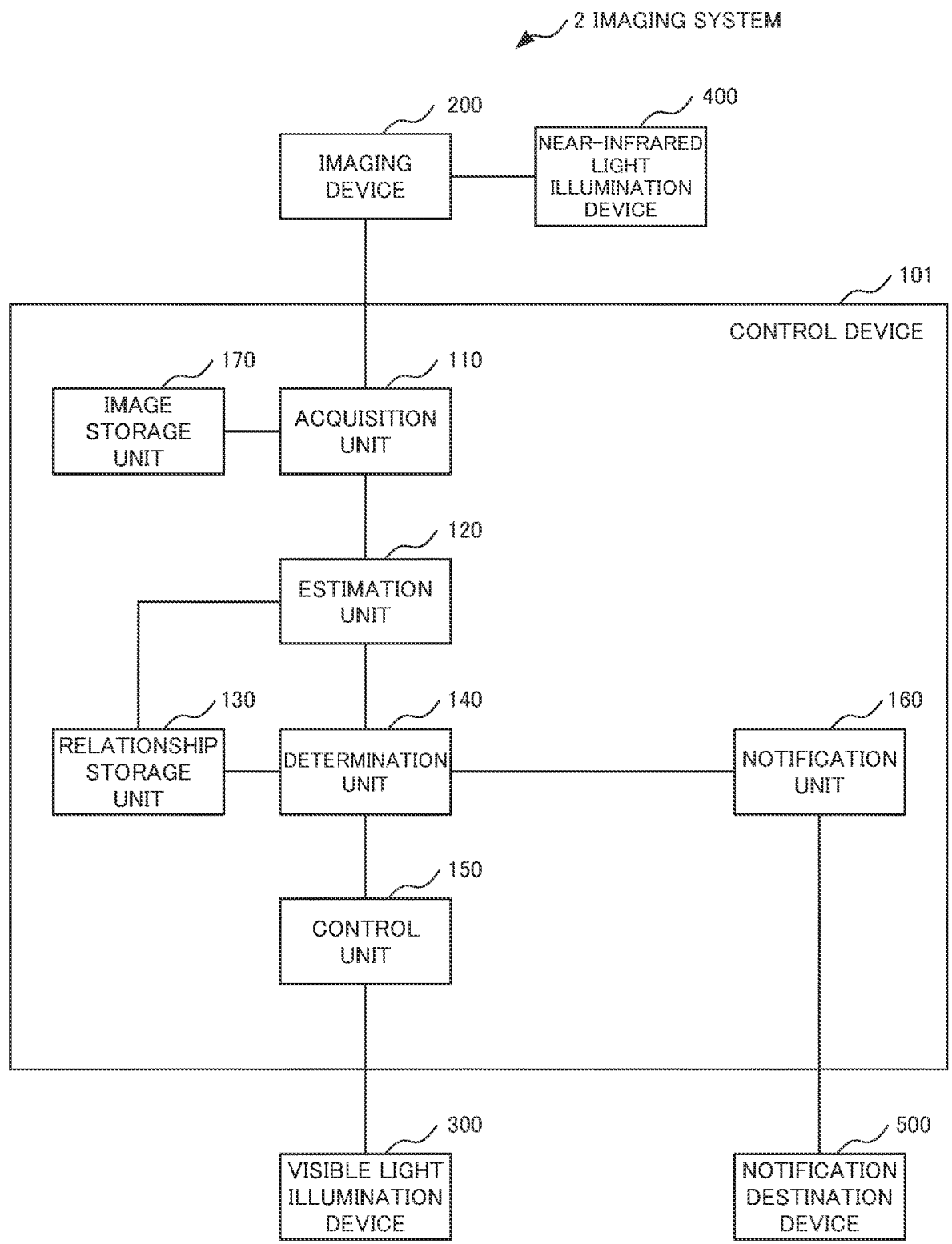
FIG. 9 is a block diagram illustrating an example of a configuration of an imaging system according to a second example embodiment of the present disclosure.

FIG. 9 is a block diagram illustrating an example of a configuration of an imaging system 2 according to the present example embodiment. The imaging system 2 is the same as the imaging system 1 of the first example embodiment except for differences to be described below.

The imaging system 2 includes a control device 101 instead of the control device 100. The control device 101 is the same as the control device 100 of the first example embodiment except for differences to be described below.

In the control device 101, an estimation unit 120 is connected to a relationship storage unit 130. The estimation unit 120 of the present example embodiment is the same as the estimation unit 120 of the first example embodiment except for differences to be described below.

The estimation unit 120 extracts a pupil region from the image (that is, input image) acquired by the acquisition unit 110. The estimation unit 120 may extract the pupil region according to any of various existing methods of extracting a pupil region. The estimation unit 120 estimates the pupil size in the eye portion on the basis of imaging information (particularly, camera parameters) of the imaging device 200. Specifically, the estimation unit 120 may estimate the pupil size on the basis of a focus position of the imaging device 200, an angle of view of the imaging device 200, a size of the image captured by the imaging device 200 (that is, the number of vertical pixels and the number of horizontal pixels), and the number of pixels in a diameter of a pupil region in the input image. The estimation unit 120 may read an illuminance size relationship from the relationship storage unit 130. The estimation unit 120 estimates illuminance of the eye portion from the estimated pupil size on the basis of the illuminance size relationship.

<<Operation>>

The control device 101 of the present example embodiment performs the same operation as the operation of the control device 100 of the first example embodiment illustrated in FIG. 3, except for the following differences.

In the present example embodiment, in step S102, the estimation unit 120 extracts the pupil region from the acquired input image. The estimation unit 120 estimates the pupil size of the extracted pupil on the basis of the imaging information.

The operation of steps other than step S102 of the control device 101 of the present example embodiment is the same as the operation of the steps to which the same reference numerals are given in the control device 100 of the first example embodiment.

<<Effect>>

The present example embodiment has the same effect as the first example embodiment. The reason is the same as the reason why the effect of the first example embodiment is exhibited.

<Modification>

To the present example embodiment, the first to fifth modifications described above can be applied.

Third Example Embodiment

Next, a third example embodiment of the present disclosure will be described in detail with reference to the drawings.

<<Configuration>>

First, a configuration of a control device 102 according to the present example embodiment will be described in detail with reference to the drawings.

Figure 10:
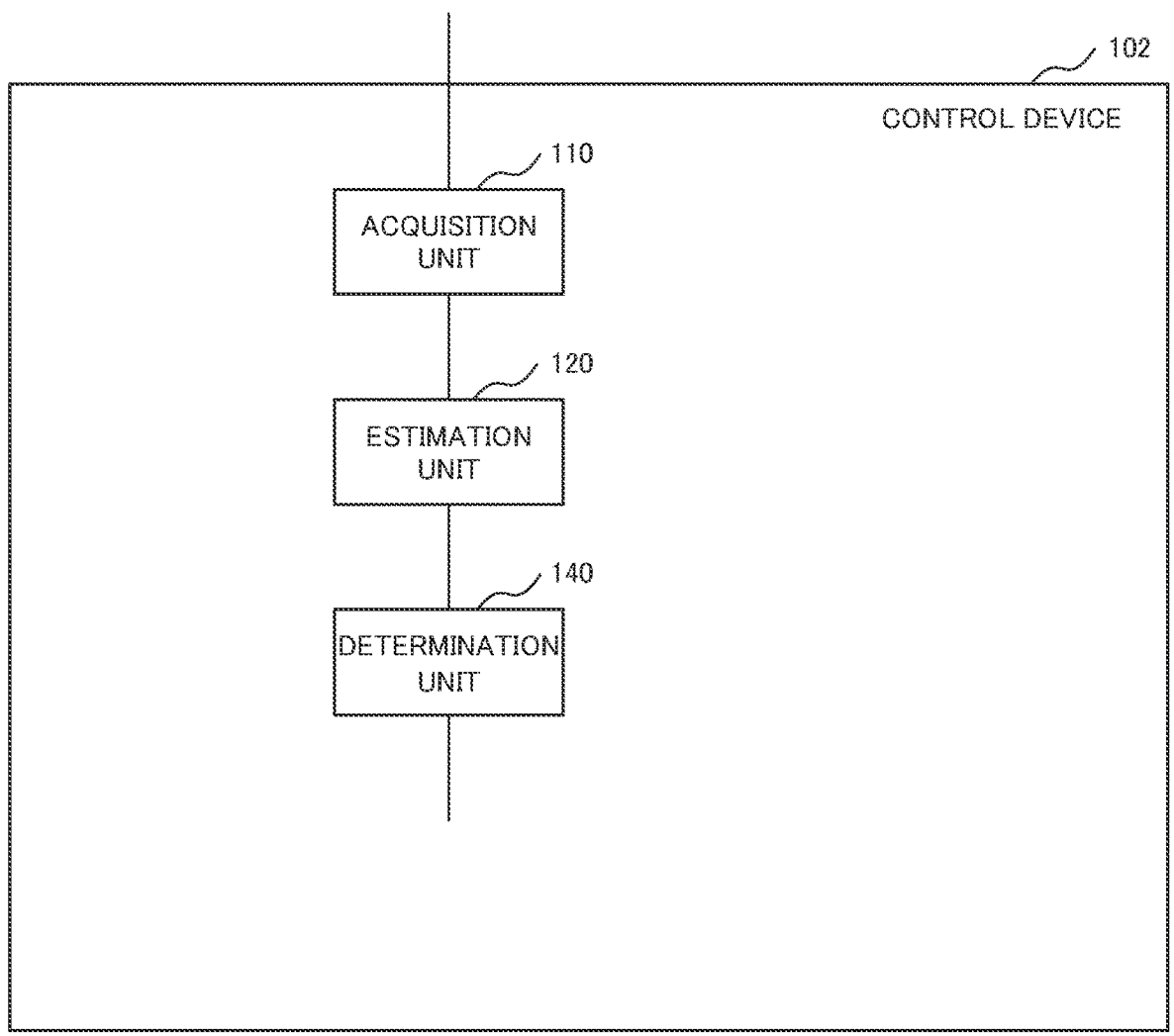
FIG. 10 is a block diagram illustrating an example of a configuration of a control device according to a third example embodiment of the present disclosure.

FIG. 10 is a block diagram illustrating an example of a configuration of the control device 102 according to the present example embodiment. In the example illustrated in FIG. 10, the control device 102 includes an acquisition unit 110, an estimation unit 120, and a determination unit 140. The acquisition unit 110 acquires an input image including an eye region, which is a region of an eye part. The estimation unit 120 estimates illuminance of the eye part from the acquired input image. The determination unit 140 determines a light amount of illumination of visible light that emits the eye part such that a pupil size of the eye part satisfies a size condition on the basis of an illuminance size relationship that is a relationship between illuminance and the pupil size.

<<Operation>>

Next, an operation of the control device 102 of the present example embodiment will be described with reference to the drawings.

Figure 11:
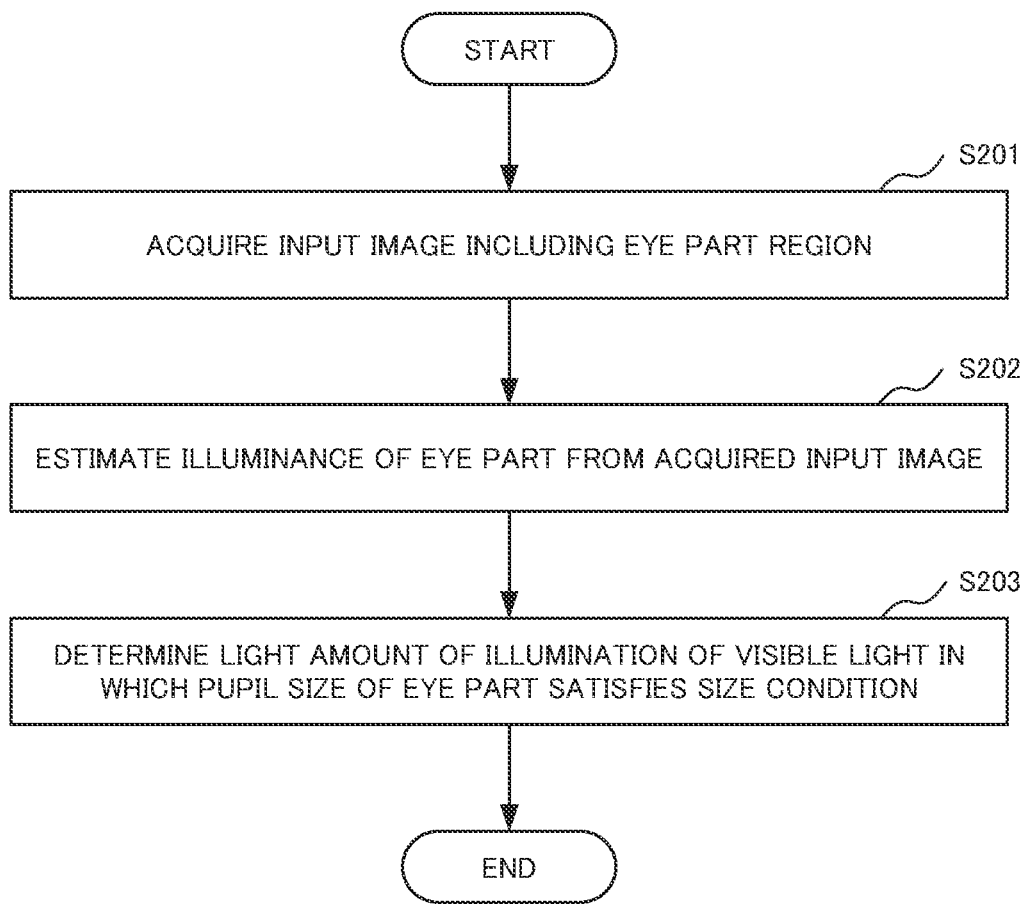
FIG. 11 is a flowchart illustrating an example of an operation of the control device according to the third example embodiment of the present disclosure.

FIG. 11 is a flowchart illustrating an example of an operation of the control device 102 according to the present example embodiment. In the operation example illustrated in FIG. 11, first, the acquisition unit 110 acquires an input image including a region of the eye part (step S201). The acquisition unit 110 may acquire the input image from, for example, the above-described imaging device 200 or an imaging device equivalent to the imaging device 200A. Next, the estimation unit 120 estimates the illuminance of the eye part from the acquired input image (step S202). The method of estimating illuminance of the eye part by the estimation unit 120 may be the same as the method of estimating illuminance of the eye part by the estimation unit 120 of the first example embodiment. The method of estimating illuminance of the eye part by the estimation unit 120 may be the same as the method of estimating illuminance of the eye part by the estimation unit 120 of the second example embodiment. Next, the determination unit 140 determines the light amount of illumination of visible light in which the pupil size of the eye part satisfies the size condition (step S203). The illumination of visible light may be the same device as the visible light illumination device 300 in the first and second example embodiments, for example. The method of determining the light amount of illumination of visible light by the determination unit 140 may be the same as the method of determining the light amount of illumination of visible light by the determination unit 140 of the first example embodiment and the determination unit 140 of the second example embodiment. In that case, the determination unit 140 may maintain the above-described illuminance size relationship.

<<Effect>>

The present example embodiment has the same effect as the first example embodiment. The reason is the same as the reason why the effect of the first example embodiment is exhibited.

Other Example Embodiments

The control device 100, the control device 101, and the control device 102 can be implemented by a computer including a memory in which a program read from a storage medium is loaded and a processor that executes the program. The control device 100, the control device 101, and the control device 102 can also be implemented by dedicated hardware. The control device 100, the control device 101, and the control device 102 can also be implemented by a combination of the above-described computer and dedicated hardware.

Figure 12:
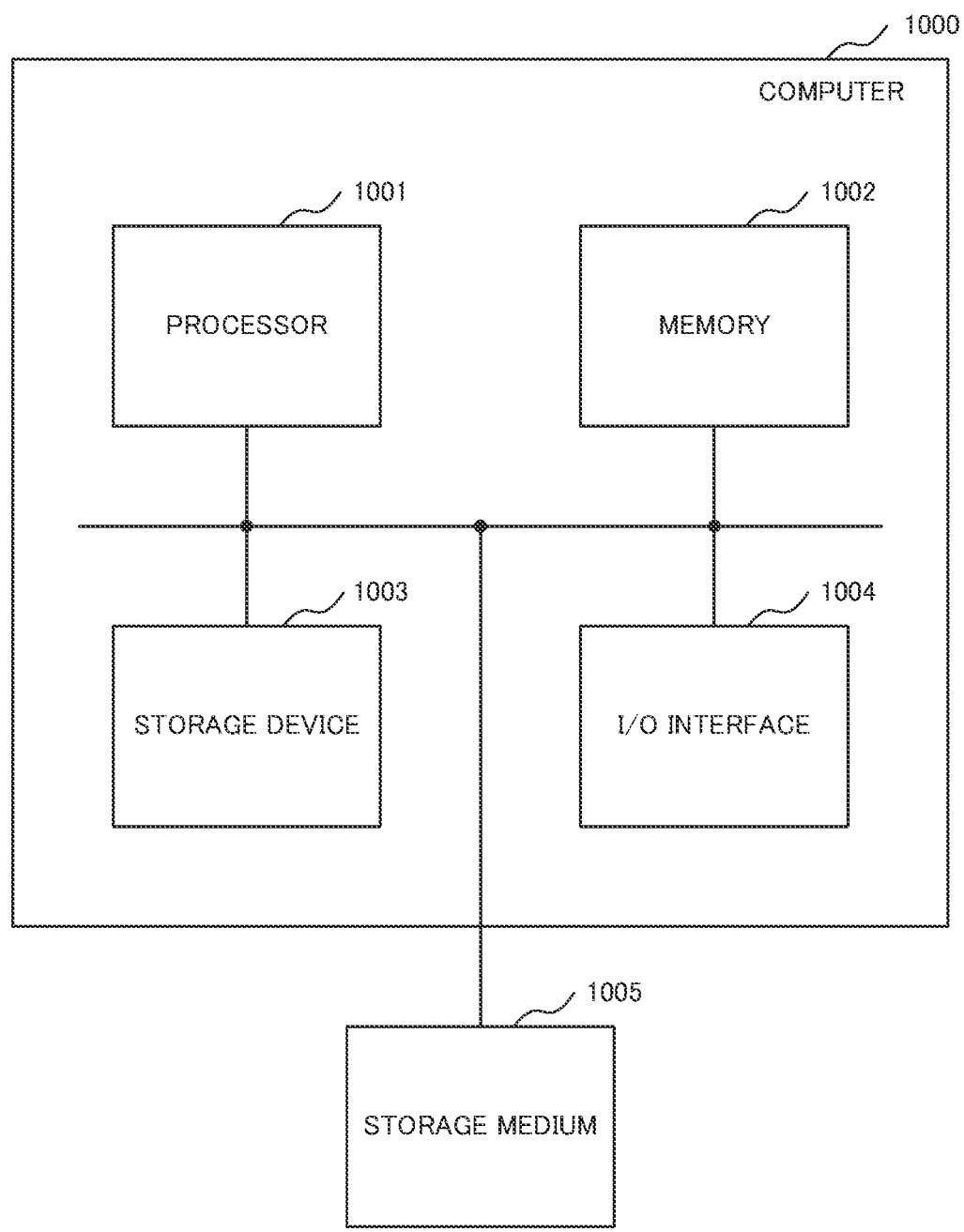
FIG. 12 is a diagram illustrating an example of a computer hardware configuration capable of implementing the control device according to the example embodiment of the present disclosure.

FIG. 12 is a diagram illustrating an example of a hardware configuration of a computer 1000 capable of implementing control devices (that is, the control device 100, the control device 101, and the control device 102) according to the above-described example embodiments. A computer 1000 illustrated in FIG. 12 includes a processor 1001, a memory 1002, a storage device 1003, and an input/output (I/O) interface 1004. Furthermore, the computer 1000 can also access a storage medium 1005. The memory 1002 and the storage device 1003 are, for example, storage devices such as a random access memory (RAM) and a hard disk. The storage medium 1005 is, for example, a storage device such as a RAM or a hard disk, a read only memory (ROM), or a portable storage medium. The storage device 1003 may be the storage medium 1005. The processor 1001 can read and write data and programs to and from the memory 1002 and the storage device 1003. The processor 1001 can access, for example, the imaging device 200, the imaging device 200A, the imaging device 200B, the visible light illumination device 300, the near-infrared light illumination device 400, the notification destination device 500, and the detection device 600 via the I/O interface 1004. The processor 1001 can access the storage medium 1005. The storage medium 1005 stores a program for operating the computer 1000 as the control devices according to the above-described example embodiments.

The processor 1001 loads, to the memory 1002, the program for operating the computer 1000 as the control devices according to the above-described example embodiments, stored in the storage medium 1005. Then, when the processor 1001 executes the program loaded in the memory 1002, the computer 1000 operates as the control devices according to the above-described example embodiments.

The acquisition unit 110, the estimation unit 120, the determination unit 140, the control unit 150, and the notification unit 160 can be implemented by, for example, the processor 1001 that executes the program loaded in the memory 1002. Furthermore, the relationship storage unit 130 and the image storage unit 170 can be implemented by the memory 1002 included in the computer 1000 and the storage device 1003 such as a hard disk device. Alternatively, some or all of the acquisition unit 110, the estimation unit 120, the relationship storage unit 130, the determination unit 140, the control unit 150, the notification unit 160, and the image storage unit 170 can be implemented by a dedicated circuit that implements the functions of the units.

<Supplementary Note>

Furthermore, some or all of the above example embodiments can be described as but are not limited to the supplementary notes below.

(Supplementary Note 1)

A control device including:

an acquisition unit which acquires an input image including an eye region that is a region of an eye part;

an estimation unit which estimates illuminance of the eye part from the acquired input image; and a determination unit which determines a light amount of illumination of visible light with which the eye part is to be irradiated in such a way that a pupil size of the eye part satisfies a size condition based on an illuminance size relationship that is a relationship between the illuminance and the pupil size.

(Supplementary Note 2)

The control device according to supplementary note 1, wherein the estimation unit detects a sclera region of the eye region from the input image, and estimates the illuminance of the eye part based on pixel information of the detected sclera region.

(Supplementary Note 3)

The control device according to supplementary note 1, wherein the estimation unit detects a pupil region of the eye region from the input image, estimates the pupil size of the eye part based on the detected pupil region, and estimates the illuminance of the eye part based on the estimated pupil size and the illuminance size relationship.

(Supplementary Note 4)

The control device according to any one of supplementary notes 1 to 3, wherein the determination unit determines, regarding illuminance of the eye region, the light amount of the illumination in such a way that a glare index determined based on the illuminance satisfies a glare condition.

(Supplementary Note 5)

The control device according to supplementary note 4, wherein the estimation unit estimates an iris color based on the acquired input image, and the determination unit selects the glare condition according to the estimated iris color.

(Supplementary Note 6)

The control device according to any one of supplementary notes 1 to 4, wherein the estimation unit estimates an iris color based on the acquired input image, and the determination unit selects, from a plurality of illuminance size relationships according to iris colors, the illuminance size relationship based on the estimated iris color, and determines the light amount of the illumination based on the selected illuminance size relationship.

(Supplementary Note 7)

The control device according to any one of supplementary notes 1 to 6, wherein the determination unit determines whether it is possible to control the light amount of the illumination in such a way that the pupil size satisfies the size condition based on the estimated illuminance and the illuminance size relationship, and the control device further includes a notification unit which sends a notification in a case where it is determined that it is not possible to control the light amount of the illumination in such a way that the pupil size satisfies the size condition.

(Supplementary Note 8)

The control device according to any one of supplementary notes 1 to 7, further including a control unit which controls the illumination in such a way that the illumination emits the visible light having the determined light amount of the illumination.

(Supplementary Note 9)

An imaging system including:

the control device according to any one of supplementary notes 1 to 8;

the illumination; and an imaging device configured to capture the input image.

(Supplementary Note 10)

A control method including:

acquiring an input image including an eye region that is a region of an eye part;

estimating illuminance of the eye part from the acquired input image; and determining a light amount of illumination of visible light with which the eye part is to be irradiated in such a way that a pupil size of the eye part satisfies a size condition based on an illuminance size relationship that is a relationship between the illuminance and the pupil size.

(Supplementary Note 11)

The control method according to supplementary note 10, further including detecting a sclera region of the eye region from the input image, and estimating the illuminance of the eye part based on pixel information of the detected sclera region.

(Supplementary Note 12)

The control method according to supplementary note 10, further including detecting a pupil region of the eye region from the input image, estimating the pupil size of the eye part based on the detected pupil region, and estimating the illuminance of the eye part based on the estimated pupil size and the illuminance size relationship.

(Supplementary Note 13)

The control method according to any one of supplementary notes 10 to 12, further including determining, regarding illuminance of the eye region, the light amount of the illumination in such a way that a glare index determined based on the illuminance satisfies a glare condition.

(Supplementary Note 14)

The control method according to supplementary note 13, further including estimating an iris color based on the acquired input image; and selecting the glare condition according to the estimated iris color.

(Supplementary Note 15)

The control method according to any one of supplementary notes 10 to 13, further including:

estimating an iris color based on the acquired input image; and selecting, from a plurality of illuminance size relationships according to iris colors, the illuminance size relationship based on the estimated iris color, and determining the light amount of the illumination based on the selected illuminance size relationship.

(Supplementary Note 16)

The control method according to any one of supplementary notes 10 to 15, further including:

determining whether it is possible to control the light amount of the illumination in such a way that the pupil size satisfies the size condition based on the estimated illuminance and the illuminance size relationship; and sending a notification in a case where it is determined that it is not possible to control the light amount of the illumination in such a way that the pupil size satisfies the size condition.

(Supplementary Note 17)

The control method according to any one of supplementary notes 10 to 16, further including controlling the illumination in such a way that the illumination emits the visible light having the determined light amount of the illumination.

(Supplementary Note 18)

A storage medium storing a program for causing a computer to execute:

acquisition processing of acquiring an input image including an eye region that is a region of an eye part;

estimation processing of estimating illuminance of the eye part from the acquired input image; and determination processing of determining a light amount of illumination of visible light with which the eye part is to be irradiated in such a way that a pupil size of the eye part satisfies a size condition based on an illuminance size relationship that is a relationship between the illuminance and the pupil size.

(Supplementary Note 19)

The storage medium according to supplementary note 18, wherein the estimation processing includes detecting a sclera region of the eye region from the input image, and estimating the illuminance of the eye part based on pixel information of the detected sclera region.

(Supplementary Note 20)

The storage medium according to supplementary note 18, wherein the estimation processing includes detecting a pupil region of the eye region from the input image, estimating the pupil size of the eye part based on the detected pupil region, and estimating the illuminance of the eye part based on the estimated pupil size and the illuminance size relationship.

(Supplementary Note 21)

The storage medium according to any one of supplementary notes 18 to 20, wherein the determination processing includes determining, regarding illuminance of the eye region, the light amount of the illumination in such a way that a glare index determined based on the illuminance satisfies a glare condition.

(Supplementary Note 22)

The storage medium according to supplementary note 21, wherein the estimation processing includes estimating an iris color based on the acquired input image, and the determination processing includes selecting the glare condition according to the estimated iris color.

(Supplementary Note 23)

The storage medium according to any one of supplementary notes 18 to 21, wherein the estimation processing includes estimating an iris color based on the acquired input image, and the determination processing includes selecting, from a plurality of illuminance size relationships according to iris colors, the illuminance size relationship based on the estimated iris color, and determining the light amount of the illumination based on the selected illuminance size relationship.

(Supplementary Note 24)

The storage medium according to any one of supplementary notes 18 to 23, wherein the determination processing includes determining whether it is possible to control the light amount of the illumination in such a way that the pupil size satisfies the size condition based on the estimated illuminance and the illuminance size relationship, and the program causes the computer to further execute notification processing of sending a notification in a case where it is determined that it is not possible to control the light amount of the illumination in such a way that the pupil size satisfies the size condition.

(Supplementary Note 25)

The storage medium according to any one of supplementary notes 18 to 24, wherein the program causes the computer to further execute control processing of controlling the illumination in such a way that the illumination emits the visible light having the determined light amount of the illumination.

While the present invention has been described with reference to the example embodiments, the present invention is not limited to these example embodiments. It will be understood by those of ordinary skill in the art that various changes in form and details of the present invention may be made therein without departing from the spirit and scope of the present invention as defined by the claims.

REFERENCE SIGNS LIST

1 Imaging system
1A Imaging system
1B Imaging system
1C Imaging system
2 Imaging system
100 Control device
101 Control device
102 Control device
110 Acquisition unit
120 Estimation unit
130 Relationship storage unit
140 Determination unit
150 Control unit
160 Notification unit
170 Image storage unit
200 Imaging device
200A Imaging device
200B Imaging device
300 Visible light illumination device
400 Near-infrared light illumination device
500 Notification destination device
600 Detection device
1000 Computer
1001 Processor
1002 Memory
1003 Storage device
1004 I/O interface
1005 Storage medium

What is claimed is:

1. A control device comprising:
at least one memory storing instructions; and
at least one processor configured to execute the instructions to:
acquire an input image including an eye region that is a region of an eye part;
estimate, from the acquired input image, illuminance of the eye part; and determine a light amount of illumination of visible light with which the eye part is irradiated in such a way that a pupil size of the eye part satisfies a size condition that the pupil size is a target size based on an illuminance size relationship between the illuminance and the pupil size, wherein the at least one processor determines, regarding the illuminance of the eye region, the light amount of the illumination in such a way that a glare index determined based on the illuminance satisfies a glare condition, the glare index is a degree of glare experienced by a person and depends on the illuminance of the eye part, and the glare condition is that the glare index does not exceed a threshold indicating a limit of permissible glare.

2. The control device according to claim 1, wherein the at least one processor is further configured to execute the instructions to:

detect a sclera region of the eye region from the input image; and estimate the illuminance of the eye part based on pixel information of the detected sclera region.

3. The control device according to claim 1, wherein the at least one processor is further configured to execute the instructions to:

detect a pupil region of the eye region from the input image;

estimate the pupil size of the eye part based on the detected pupil region; and determine the illuminance of the eye part based on the estimated pupil size and the illuminance size relationship.

4. The control device according to claim 1, wherein the at least one processor is further configured to execute the instructions to:

estimate an iris color based on the acquired input image; and select the glare condition according to the estimated iris color.

5. The control device according to claim 1, wherein the at least one processor is further configured to execute the instructions to:

estimate an iris color based on the acquired input image;

select, from a plurality of illuminance size relationships according to iris colors, the illuminance size relationship based on the estimated iris color; and determine the light amount of the illumination based on the selected illuminance size relationship.

6. The control device according to claim 1, wherein the at least one processor is further configured to execute the instructions to:

determine, based on the estimated illuminance and the illuminance size relationship, whether the light amount of the illumination is controllable in such a way that the pupil size satisfies the size condition; and send a notification in a case in which the light amount of the illumination is not controllable in such a way that the pupil size satisfies the size condition.

7. The control device according to claim 1, wherein the at least one processor is further configured to execute the instructions to control the illumination in such a way that the illumination emits the visible light having the determined light amount of the illumination.

8. An imaging system comprising:
the control device according to claim 1;
the illumination; and
an imaging device configured to capture the input image.

9. A control method performed by a computer and comprising:

acquiring an input image including an eye region that is a region of an eye part;

estimating, from the acquired input image, illuminance of the eye part; and determining a light amount of illumination of visible light with which the eye part is to be irradiated in such a way that a pupil size of the eye part satisfies a size condition that the pupil size is a target size based on an illuminance size relationship between the illuminance and the pupil size, wherein the computer determines, regarding the illuminance of the eye region, the light amount of the illumination in such a way that a glare index determined based on the illuminance satisfies a glare condition, the glare index is a degree of glare experienced by a person and depends on the illuminance of the eye part, and the glare condition is that the glare index does not exceed a threshold indicating a limit of permissible glare.

10. The control method according to claim 9, further comprising:

detecting a sclera region of the eye region from the input image and estimating the illuminance of the eye part based on pixel information of the detected sclera region.

11. The control method according to claim 9, further comprising:

detecting a pupil region of the eye region from the input image;

estimating the pupil size of the eye part based on the detected pupil region;

and estimating the illuminance of the eye part based on the estimated pupil size and the illuminance size relationship.

12. The control method according to claim 9, further comprising:

estimating an iris color based on the acquired input image; and selecting the glare condition according to the estimated iris color.

13. The control method according to claim 9, further comprising:

estimating an iris color based on the acquired input image; and selecting, from a plurality of illuminance size relationships according to iris colors, the illuminance size relationship based on the estimated iris color;

and determining the light amount of the illumination based on the selected illuminance size relationship.

14. The control method according to claim 9, further comprising:

determining, based on the estimated illuminance and the illuminance size relationship, whether the light amount of the illumination is controllable in such a way that the pupil size satisfies the size condition; and sending a notification in a case in which the light amount of the illumination is not controllable in such a way that the pupil size satisfies the size condition.

15. The control method according to claim 9, further comprising controlling the illumination in such a way that the illumination emits the visible light having the determined light amount of the illumination.

16. A non-transitory computer readable storage medium storing a program executable by a computer to perform processing comprising:

acquiring an input image including an eye region that is a region of an eye part;

estimating, from the acquired input image, illuminance of the eye part; and determining a light amount of illumination of visible light with which the eye part is to be irradiated in such a way that a pupil size of the eye part satisfies a size condition that the pupil size is a target size based on an illuminance size relationship between the illuminance and the pupil size, wherein the computer determines, regarding the illuminance of the eye region, the light amount of the illumination in such a way that a glare index determined based on the illuminance satisfies a glare condition, the glare index is a degree of glare experienced by a person and depends on the illuminance of the eye part, and the glare condition is that the glare index does not exceed a threshold indicating a limit of permissible glare.

17. The storage medium according to claim 16, wherein the processing further comprises:

detecting a sclera region of the eye region from the input image; and estimating the illuminance of the eye part based on pixel information of the detected sclera region.

18. The storage medium according to claim 16, wherein the processing further comprises:

detecting a pupil region of the eye region from the input image;

estimating the pupil size of the eye part based on the detected pupil region; and estimating the illuminance of the eye part based on the estimated pupil size and the illuminance size relationship.

* * * * *